(12) United States Patent
Akimoto et al.

(10) Patent No.: US 7,929,014 B2
(45) Date of Patent: *Apr. 19, 2011

(54) INSERTION SUPPORT SYSTEM

(75) Inventors: Shunya Akimoto, Kawasaki (JP);
Junichi Ohnishi, Hachioji (JP)

(73) Assignee: Olympus Corporation, Tokyo (JP)

( * ) Notice: Subject to any disclaimer, the term of this patent is extended or adjusted under 35 U.S.C. 154(b) by 1391 days.

This patent is subject to a terminal disclaimer.

(21) Appl. No.: 11/414,674

(22) Filed: Apr. 28, 2006

(65) Prior Publication Data

US 2006/0203089 A1    Sep. 14, 2006

Related U.S. Application Data

(63) Continuation of application No. PCT/JP2004/016232, filed on Nov. 1, 2004.

(30) Foreign Application Priority Data

Nov. 4, 2003 (JP) ................................. 2003-374929

(51) Int. Cl.
*A61B 1/00* (2006.01)
*A62B 1/04* (2006.01)

(52) U.S. Cl. .......................................... 348/65; 600/104

(58) Field of Classification Search .................. 600/104, 600/114, 124, 188; 345/427; 348/65
See application file for complete search history.

(56) References Cited

U.S. PATENT DOCUMENTS

| | | | | |
|---|---|---|---|---|
| 5,702,348 A | * | 12/1997 | Harhen | 600/124 |
| 6,346,940 B1 | * | 2/2002 | Fukunaga | 345/427 |
| 6,652,453 B2 | * | 11/2003 | Smith et al. | 600/188 |
| 7,473,219 B1 | * | 1/2009 | Glenn | 600/114 |
| 2004/0039250 A1 | * | 2/2004 | Tholfsen et al. | 600/104 |

FOREIGN PATENT DOCUMENTS

| | | |
|---|---|---|
| EP | 1 466 552 A1 | 10/2004 |
| EP | 1 681 011 A1 | 7/2006 |
| JP | 2000-135215 | 5/2000 |
| JP | 2004-089483 | 3/2004 |

OTHER PUBLICATIONS

Supplementary European Search Report dated Jan. 26, 2010.

* cited by examiner

*Primary Examiner* — Gims S Philippe
(74) *Attorney, Agent, or Firm* — Scully, Scott, Murphy & Presser, P.C.

(57) ABSTRACT

With a bronchial tube insertion support system according to the present invention, a route setting unit comprises a route starting-point setting function for setting the insertion starting-point of a bronchial tube, a region-of-interest setting function for setting a region of interest serving as the insertion end-point of the bronchial tube, a route extracting function for extracting an insertion route from an insertion start point to an insertion end point, and a route verifying function for performing verification of the extracted insertion route. According to these functions, of multiple insertion routes, the most appropriate insertion route when performing insertion support is determined.

4 Claims, 40 Drawing Sheets

VOLUME DATA DISPLAY

INSERTION SUPPORT SYSTEM

CROSS REFERENCE TO RELATED APPLICATION

This application is a continuation application of PCT/JP2004/016232 filed on Nov. 1, 2004 and claims benefit of Japanese Application No. 2003-374929 filed in Japan on Nov. 4, 2003, the entire contents of which are incorporated herein by this reference.

BACKGROUND OF THE INVENTION

1. Field of the Invention

The present invention relates to an insertion support system for supporting insertion of an endoscope.

2. Description of the Related Art

In recent years, diagnosis using images has been widely performed; for example, diagnosis of a target portion has been performed using three-dimensional image data obtained within a subject by capturing tomograms of the subject using an X-ray CT (Computed Tomography) apparatus or the like.

With CT apparatuses, spiral consecutive scan (helical scan) is performed regarding a three-dimensional region of a subject by consecutively forwarding the subject in the body-axial direction while consecutively rotating X-ray radiation and detection, thereby creating a three-dimensional image from consecutive sliced tomograms of the three-dimensional region.

One example of such three-dimensional images is three-dimensional images of the bronchial tube of the lungs. The three-dimensional images of the bronchial tube are used for three-dimensionally recognizing the position of an abnormal portion where lung cancer or the like is suspected, for example. In order to confirm the abnormal portion using a biopsy, sampling of tissue samples (samples) is performed by inserting a bronchoscope and projecting a biopsy needle or biopsy forceps or the like from the tip thereof.

With ducts within the body having multistage branches like the bronchial tubes, it is difficult for the tip of the endoscope to accurately reach a target portion in a short time when the position of the abnormal portion is close to distal ducts, so with Japanese Unexamined Patent Application Publication No. 2000-135215 and the like for example, a device for navigating a bronchoscope to the target portion has been proposed by creating a three-dimensional image of a duct within the subject based on the image data of a three-dimensional region of the subject, obtaining the route to the target point along the duct on the three-dimensional image, creating a virtual endoscopic image of the duct along the route based on the image data, and displaying the virtual endoscopic image.

SUMMARY OF THE INVENTION

An insertion support system according to the present invention comprises virtual image generating means for generating a virtual image of the body cavity path within a subject based on the image data of a three-dimensional region of the subject, route starting-point setting means for setting the starting-point of an insertion route of an endoscope to the body cavity path within the subject, region-of-interest setting means for setting the region of a portion of interest within the subject, route extracting means for extracting the multiple insertion routes to the region of the portion of interest from the starting-point, and route verifying means for verifying the multiple insertion routes extracted by the route extracting means.

DETAILED DESCRIPTION OF THE PREFERRED EMBODIMENT(S)

Hereinafter, description will be made regarding embodiments of the present invention with reference to the drawings.

First Embodiment

Figure 1:
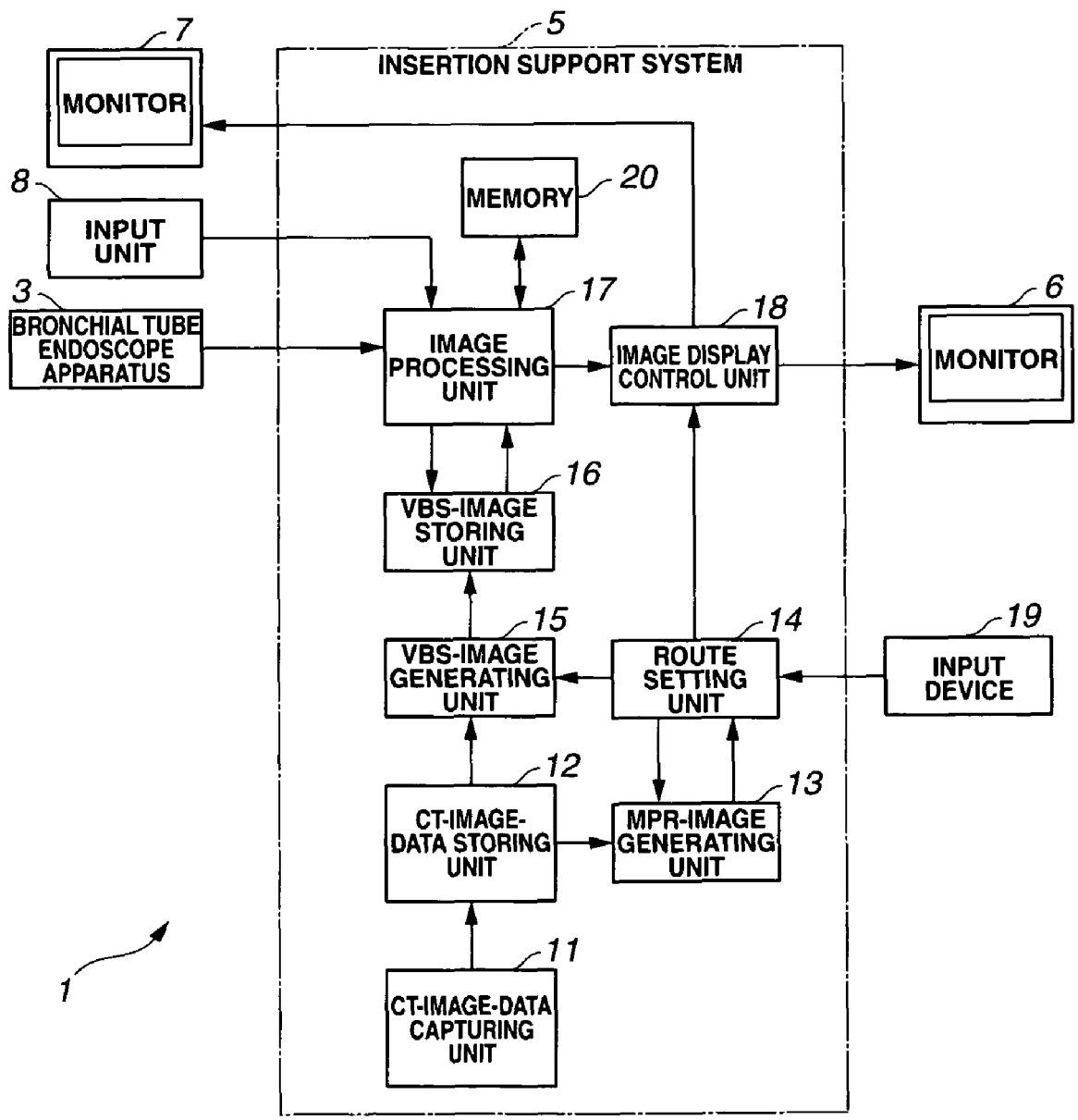
FIG. 1 is a configuration diagram illustrating the configuration of a bronchial tube insertion support system according to a first embodiment of the present invention.

As shown in FIG. 1, a bronchial tube insertion support system 1 according to the present embodiment has a bronchoscope apparatus 3 and an insertion support device 5.

The insertion support device 5 generates a virtual endoscopic image within a bronchial tube (hereinafter, referred to as VBS image) based on CT image data, and also synthesizes the endoscope image obtained by the bronchoscope apparatus 3 (hereinafter, referred to as live image) and the VBS image to display this on a monitor 6, thereby performing insertion support of the bronchoscope apparatus 3 to the bronchial tube.

Also, the bronchoscope apparatus 3, though not shown in the drawing, has a bronchoscope having image capturing means, a light source for supplying illumination light to the bronchoscope, a camera control unit for subjecting an image-captured signal from the bronchoscope to signal processing, and so forth, inserts the bronchoscope in the bronchial tube within a patient to capture an image within the bronchial tube, subjects the target tissue of the end of the bronchial tube to biopsy, and also synthesizes a live image and a VBS image to display this on a monitor 7.

With the monitor 7, an input unit 8 made up of a touch panel is provided, and a user can operate the input unit 8 made up of a touch panel while performing insertion procedure.

The insertion support device 5 has a CT-image-data capturing unit 11 for capturing the three-dimensional image data generated at an unshown known CT device for capturing X-ray tomograms of a patient via a portable storage medium such as a MO (Magnetic Optical disk) device, or DVD (Digital Versatile Disk) device, a CT-image-data storing unit 12 for storing CT image data captured by the CT-image-data capturing unit 11, an MPR-image generating unit 13 for generating MPR images (multistage restructuring images: coronal image, axial image, and sagittal image) based on the CT image data stored in the CT-image-data storing unit 12, a route setting unit 14 for generating a later-described route setting screen having the MPR image generated by the MPR-image generating unit to set a support route of the bronchoscope apparatus 3 to the bronchial tube (hereinafter, simply referred to as route), a VBS-image generating unit 15 serving as virtual image generating means for generating VBS images for each frame wherein the routes set by the route setting unit 14 based on the CT image data stored in the CT-image-data storing unit 12 continue, a VBS-image storing unit 16 for storing the VBS images generated by the VBS-image generating unit 15, an image processing unit 17 for inputting the image-captured signal from the bronchoscope apparatus 3 and the input signal from the input unit 8, and generating a later-described insertion support screen made up of a live image, a VBS image, and multiple thumbnail VBS images, an image display control unit 18 for displaying the route setting screen generated by the route setting unit 14 and the insertion support screen generated by the image processing unit 17 on the monitor 6, and an input device 19 made up of a keyboard and pointing device for inputting setting information to the route setting unit 14.

The bronchoscope apparatus 3 receives the VBS image and thumbnail VBS image from the image processing unit 17 of the insertion support device 5 to synthesize these with a live image, displays the screen equivalent to the insertion support screen, which the insertion support device 5 displays on the monitor 6, on the monitor 7. Also, the bronchoscope apparatus 3 outputs the input information from the input unit 8 made up of the touch sensor of the monitor 7 to the image processing unit 17 of the insertion support device 5.

Note that the CT-image-data storing unit 12 and the VBS-image storing unit 16 may be configured of one hard disk, and also the MPR-image generating unit 13, route setting unit 14, VBS-image generating unit 15, and image processing unit 17 may be configured of one arithmetic processing circuit. Also, an arrangement has been made wherein the CT-image-data capturing unit 11 captures CT image data via a portable storage medium such as an MO or DVD, but in the event that a CT device or in-hospital server storing CT image data is connected to an in-hospital LAN, CT image data may be captured via the in-hospital LAN by comprising the CT-image-data capturing unit 11 using an interface circuit capable of connecting to the in-hospital LAN.

Figure 2:
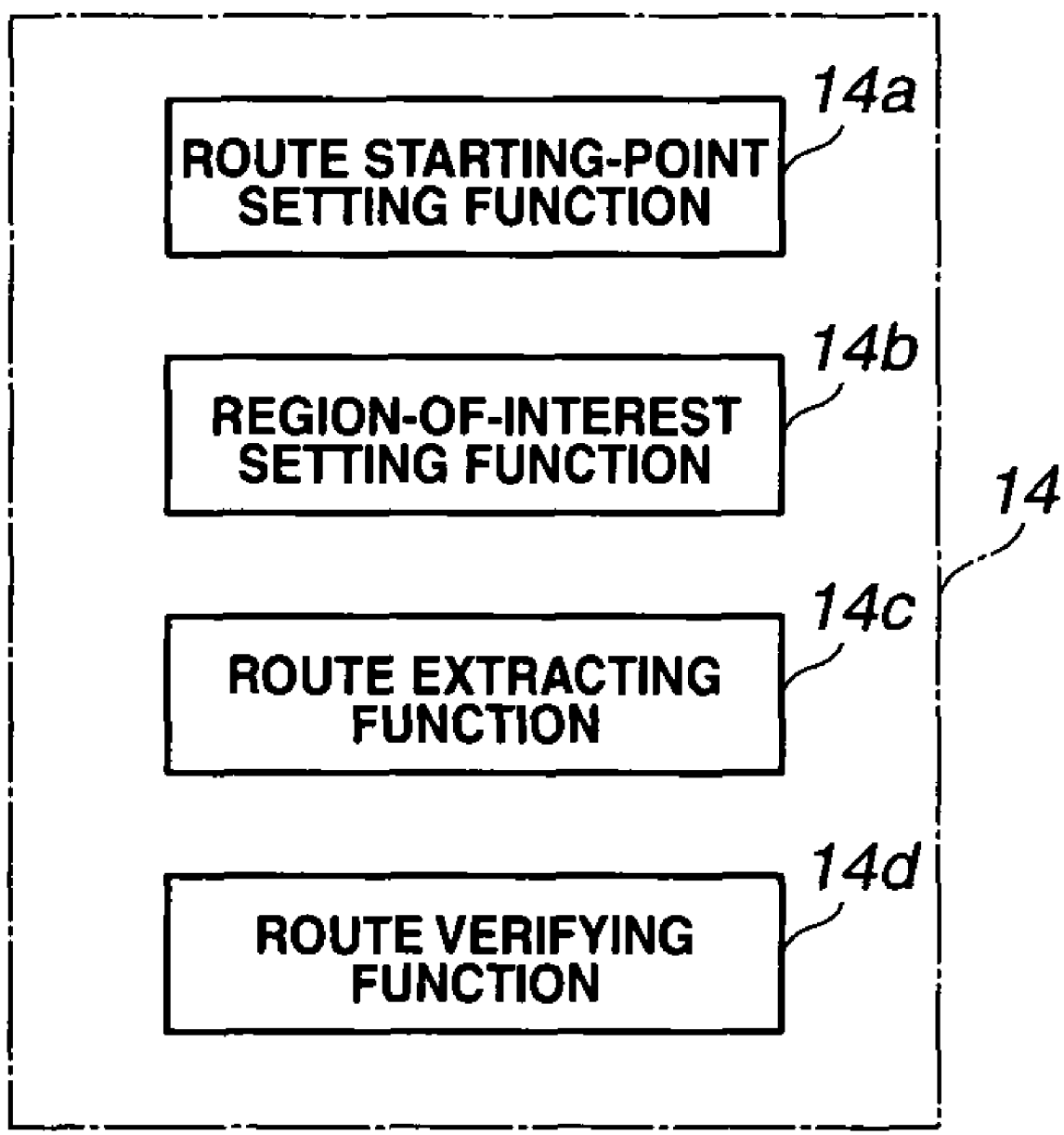
FIG. 2 is a block diagram illustrating the functional configuration of the route setting unit in FIG. 1.

The route setting unit 14, as shown in FIG. 2, has a route starting-point setting function 14a serving as route starting-point setting means for setting the insertion starting-point of the bronchial tube, a region-of-interest setting function 14b serving as region-of-interest setting means for setting a region of interest serving as the insertion end-point of the bronchial tube, a route extracting function 14c serving as route extracting means for extracting an insertion route to the insertion end-point from the insertion starting-point, and a route verifying function 14d serving as route verifying means for performing verification of the extracted insertion route. Detailed description of these functions will be given later.

Description will be made regarding operation of the present embodiment thus configured.

Figure 3:
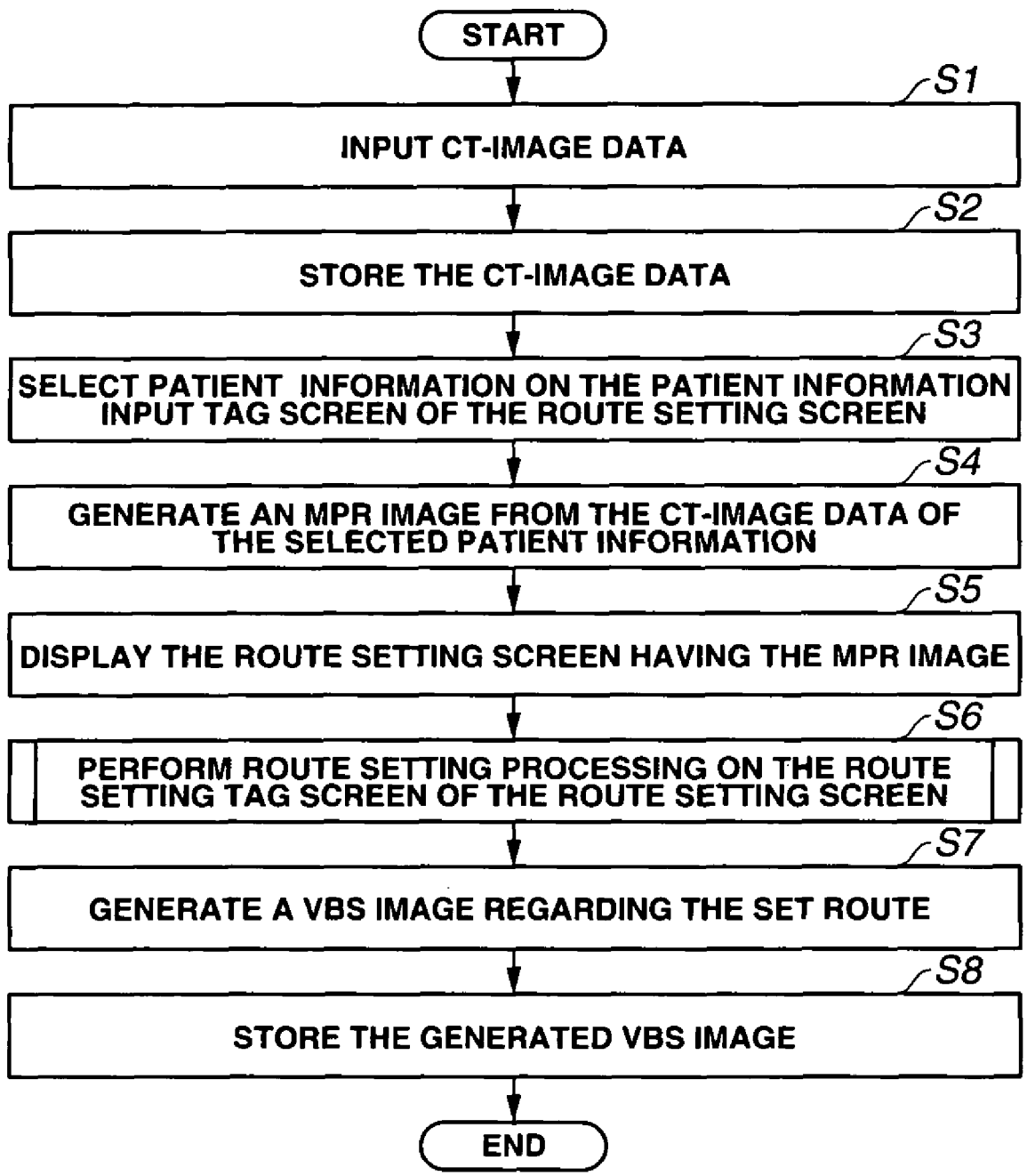
FIG. 3 is a flowchart illustrating the flow of insertion support preparation processing using the insertion support device in FIG. 1.

As shown in FIG. 3, prior to observation and treatment using the bronchoscope apparatus 3, the insertion support device 5 captures the CT image data of a patient generated at the CT device using the CT-image-data capturing unit 11 in step S1, and stores the captured CT image data in the CT-image-data storing unit 12 in step S2.

Figure 4:
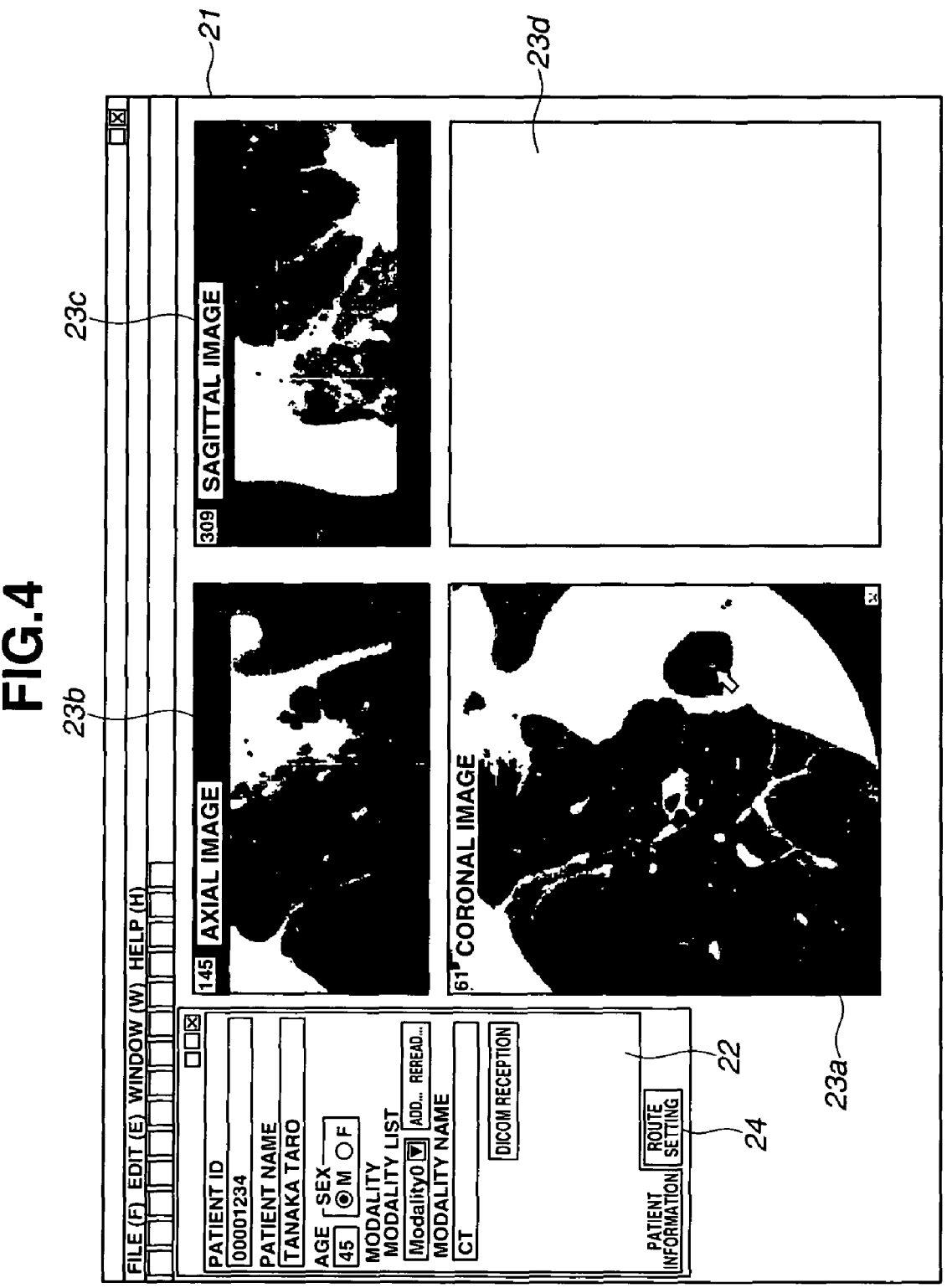
FIG. 4 is a first diagram illustrating the route setting screen to be developed in the processing in FIG. 3.

In step S3, the route setting unit 14 displays a route setting screen 21 such as shown in FIG. 4 on the monitor 6, and lets the user select patient information at a patient information tag screen 22 on the route setting screen 21. According to this selection, in step S4, the MPR-image generating unit generates, for example, a coronal image 23a, axial image 23b, and sagittal image 23c serving as MPR images (hereinafter, simply referred to as MPR images 23) made up of three different multistage restructuring images of the selected patient, and these coronal image 23a, axial image 23b, and sagittal image 23c are displayed on the route setting screen 21 in step S5. On the route setting screen 21 a VBS image display area 23d for displaying a VBS image is provided.

Note that selection of patient information at the patient information tag screen 22 is performed by the user inputting a patient ID for identifying a patient through the input device 19.

Figure 5:
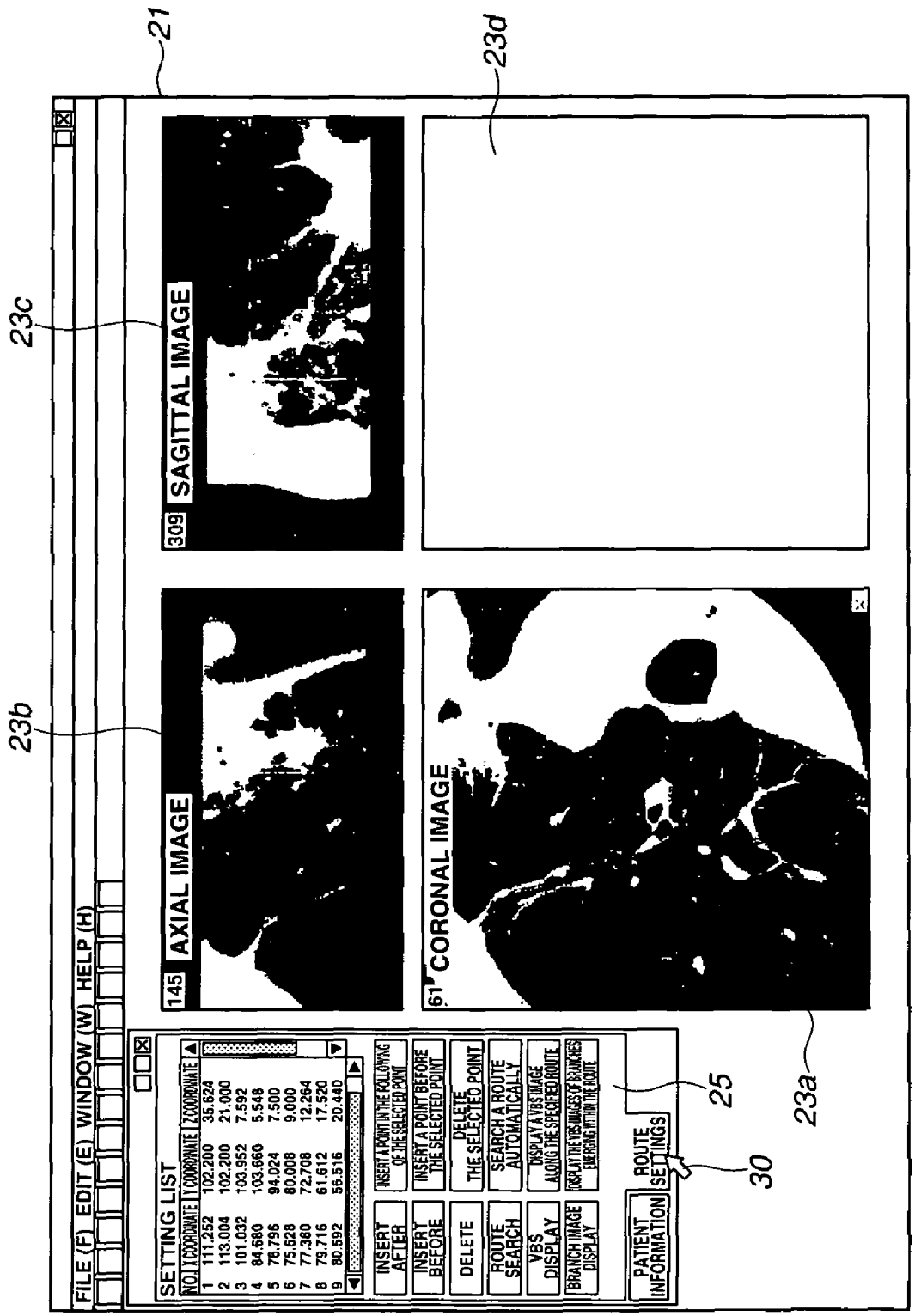
FIG. 5 is a second diagram illustrating the route setting screen to be developed in the processing in FIG. 3.

Next, in step S6, upon the user selecting a route setting tag 24 (see FIG. 4) on the route setting screen 21 through the input device 19, a route setting tag screen 25 such as shown in FIG. 5 is displayed on the route setting screen 21, the route setting unit 14 performs later-described route setting processing, and sets the insertion support route of the bronchoscope at the bronchial tube.

Upon the insertion support route having been set, the VBS-image generating unit 15 generates the VBS images for each frame wherein all of the set routes continue in step S7, and stores the generated VBS images in the VBS-image storing unit 16 in step S8.

According to the above processing in steps S1 through S8, insertion support preparation by the insertion support device 4 is completed at the time of observation and treatment using the bronchoscope.

Now, description will be made regarding the route setting processing in the above step S6 with reference to FIGS. 6 through 9.

Figure 6:
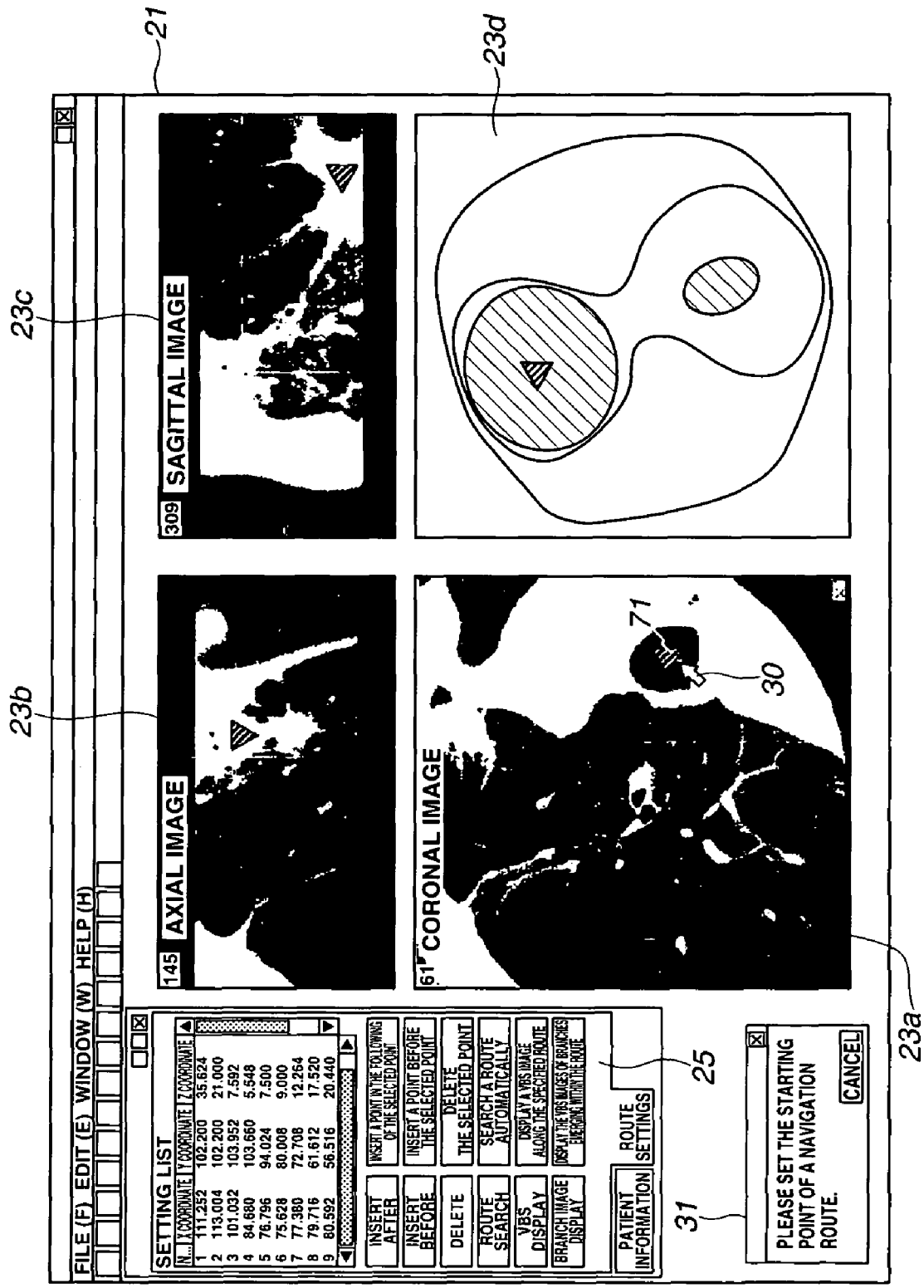
FIG. 6 is a third diagram illustrating the route setting screen to be developed in the processing in FIG. 3.

Upon the user selecting a route search button on the route setting screen 21, the route setting processing in step S6 starts. Specifically, the route starting-point setting function 14a of the route setting unit 14 displays a starting-point input-instruction window 31 for prompting the user to input the starting point of a route such as shown in FIG. 6 on the route setting screen 21. Subsequently, the user specifies a starting point 71 on one tomogram of the MPR images 23 using a cursor 30 on the route setting screen 21. Upon the user specifying the starting point 71, the starting point 71 is set on the corresponding positions of the two tomograms of the other MPR images 23, and also the VBS image at the starting point 71 is displayed on the VBS image display area 23d, and then a biopsy area input-instruction window 32 for prompting the user to set a biopsy area 72 serving as the end point of a route such as shown in FIG. 7 is displayed on the route setting screen 21.

Next, according to the region-of-interest setting function 14b of the route setting unit 14, the user two-dimensionally traces and sets the biopsy area 72 serving as a region of interest on any one of two tomograms of the MPR images 23 by operating the cursor 30 on the route setting screen 21 in this FIG. 6. The number of the biopsy areas 72 is not restricted to one, so multiple biopsy areas 72 can be specified, and FIG. 7 illustrates a state in which two biopsy areas 72a and 72b are specified.

Figure 8:
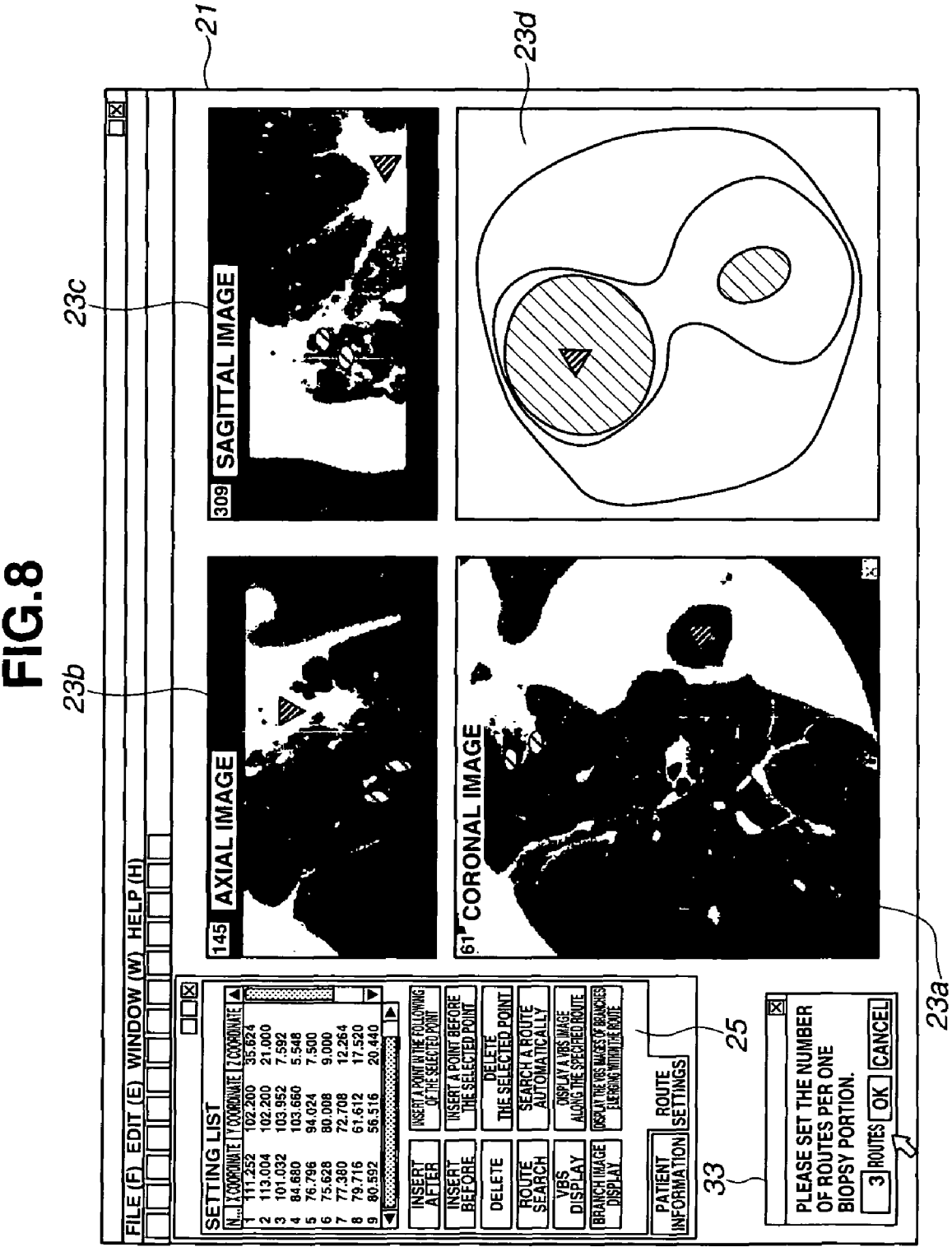
FIG. 8 is a fifth diagram illustrating the route setting screen to be developed in the processing in FIG. 3.

Subsequently, upon the user completing setting of the biopsy areas 72, the route extracting function 14c of the route setting unit 14 displays a route number setting window 33 for setting the number of routes to be searched per one biopsy area 72 such as shown in FIG. 8 on the route setting screen 21. Multiple approach routes to the biopsy area 72 to be navigated are searched by setting the number of search routes per one biopsy area 72.

Figure 7:
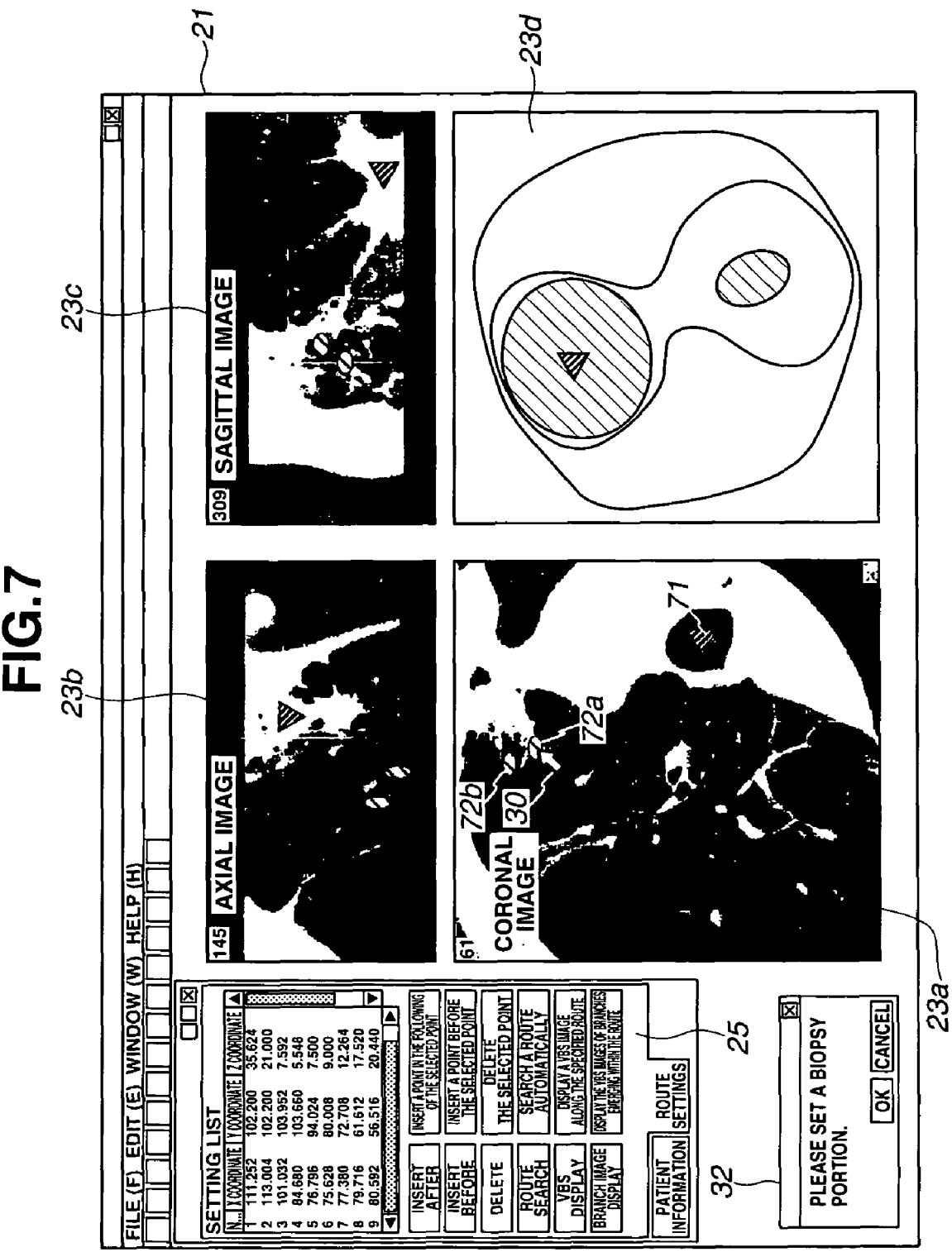
FIG. 7 is a fourth diagram illustrating the route setting screen to be developed in the processing in FIG. 3.
Figure 9:
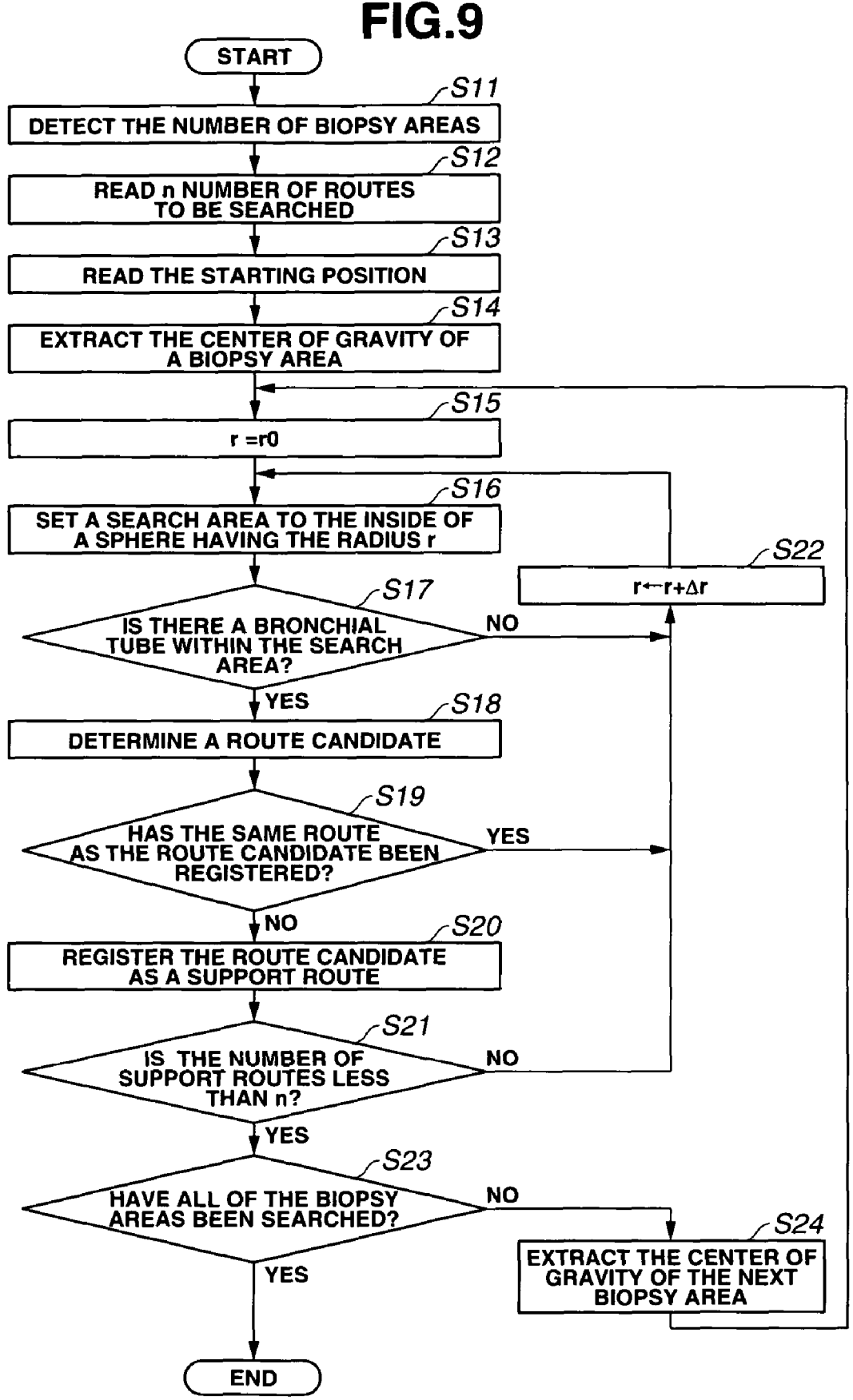
FIG. 9 is a flowchart illustrating the flow of the route setting processing in FIG. 3.

That is to say, upon the user setting the staring point, biopsy area 72, and the number of search routes through FIG. 6 through FIG. 8, the route extracting function 14c searches the routes in accordance with processing in FIG. 9.

That is to say, as shown in FIG. 9, the route extracting function 14c detects the number of the biopsy areas 72 set in step S11, reads a number n of search routes in step S12, and reads the position of the starting point 71 in step S13.

Subsequently, the route extracting function 14c extracts the center-of-gravity position of each biopsy area 72 in step S14, sets r representing the radius of a sphere centered on the center-of-gravity position to an initial value r0 in step S15, and then specifies the inside of the sphere having the radius r as a search area in step S16.

The route extracting function 14c determines whether or not there is the bronchial tube within the search area in step S17, and in the event that there is the bronchial tube, determines a route candidate wherein the position thereof is taken as an end point in step S18.

Upon the route candidate being determined, the route extracting function 14c determines whether or not the route candidate determined in step S19 has been registered, and in the event of the route candidate being unregistered, the route extracting function 14c generates a route name based on the branch name from the starting point to the end point in step S20 to register this as a support route.

Subsequently, in step S21 the route extracting function 14c determines whether or not the number of routes registered is less than the n number of routes read in step S12.

Note that in the event that the route extracting function 14c determines that there is no bronchial tube within the search area in step S17, or in the event that the route candidate determined in step S19 has been registered, or in the event of the number of routes registered being less than the n number of routes in step S21, in step S22 the route extracting function 14c enlarges the search area by adding Δr to r, and returns to step S16.

Upon the number of routes registered reaching the n number of routes read in step S2, the route extracting function 14c determines whether or not all of the biopsy areas set have been searched in step S23, and in the event of all of the biopsy areas having been searched, ends the processing, and in the event of unsearched biopsy areas having been left, extracts the center-of-gravity position of the next biopsy area in step S23, and returns to step S15.

Figure 10:
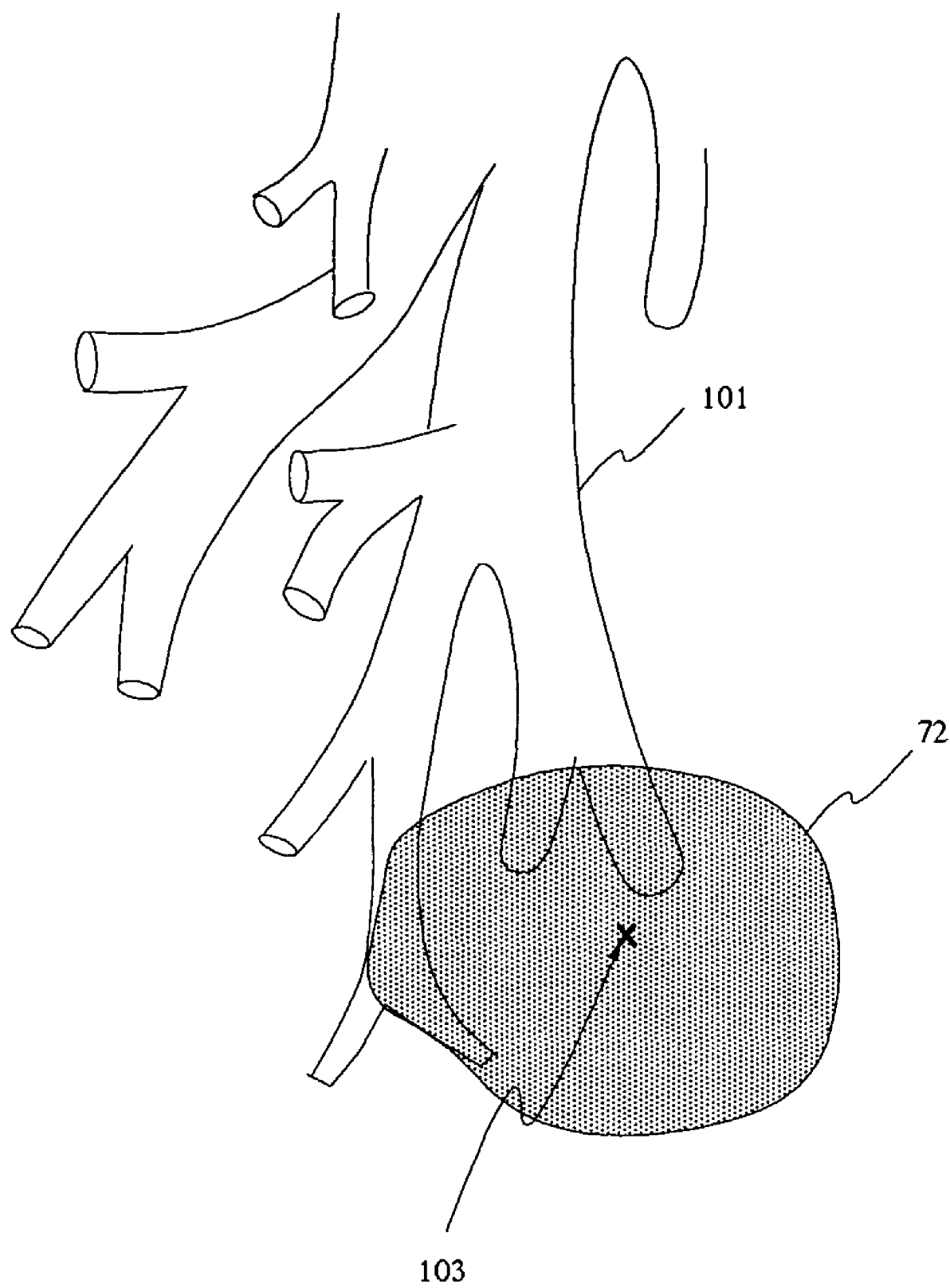
FIG. 10 is a first diagram describing the processing in FIG. 9.

Specifically, as shown in FIG. 10, upon the user specifying the biopsy area 72 at the end portion of the bronchial tube 101, the route extracting function 14c extracts the center of gravity 103 of the biopsy area 72.

Figure 11:
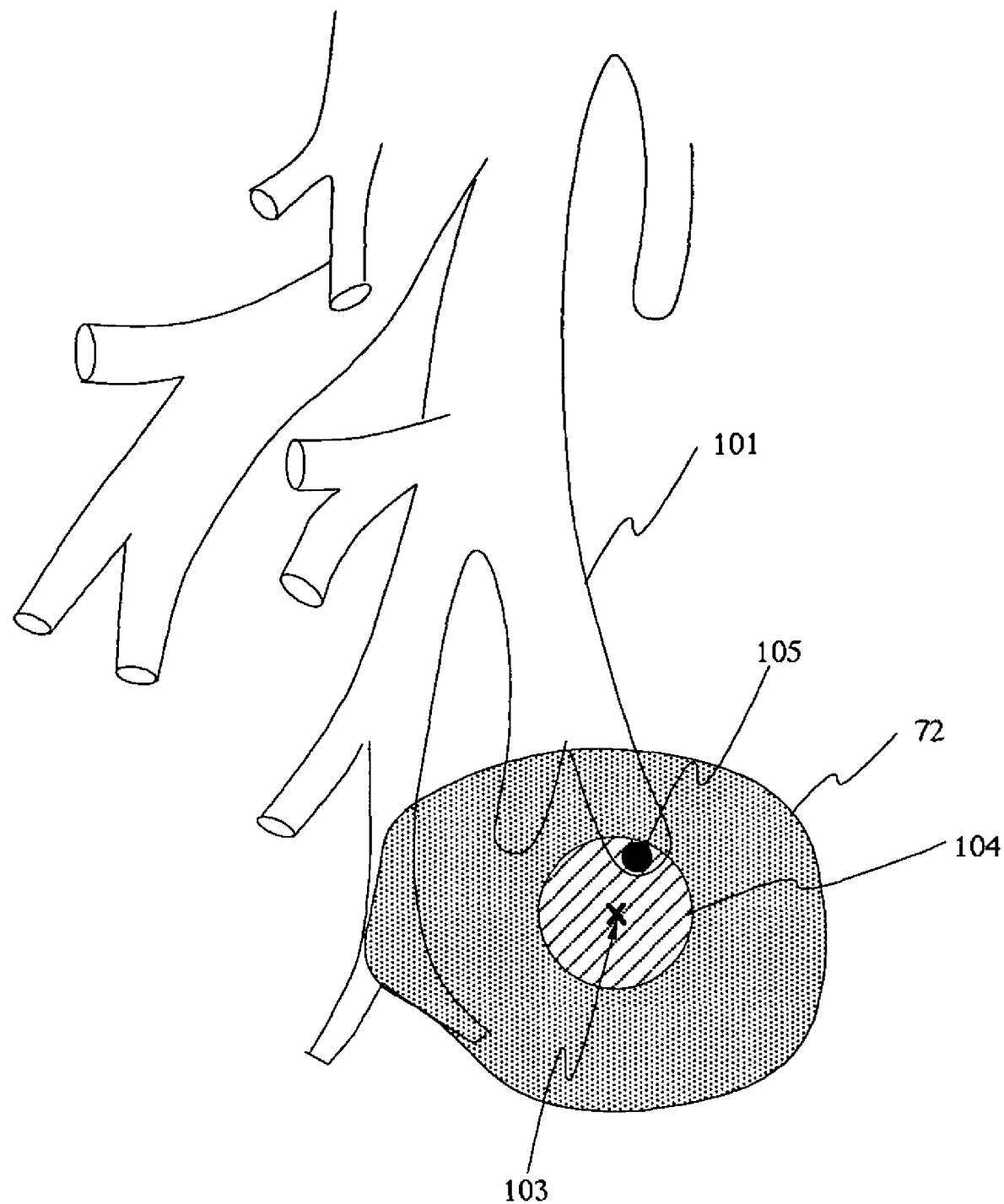
FIG. 11 is a second diagram describing the processing in FIG. 9.
Figure 12:
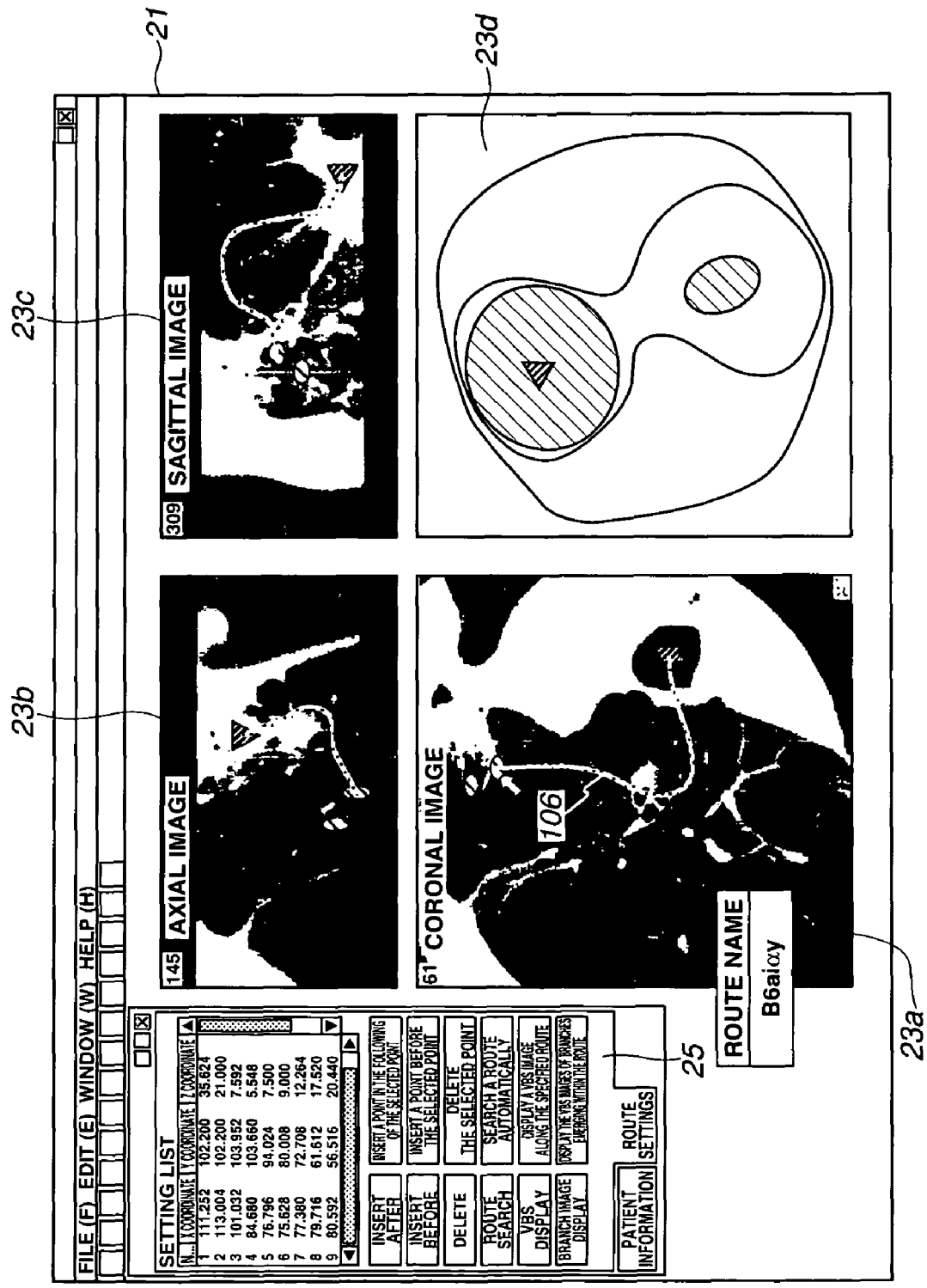
FIG. 12 is a first diagram illustrating the route setting screen to be developed in the processing in FIG. 9.

Subsequently, as shown in FIG. 11, the route extracting function 14c takes the circle centered on this center of gravity 103 as a search area 104, enlarges the search area 104 until the bronchial tube is positioned within the search area 104, and takes the point where the bronchial tube is positioned first within the search area 104 as an end point 105. Subsequently, the route extracting function 14c determines a first route candidate 106 connecting the starting point 71 and this end point 105 as shown in FIG. 12. In the event of this first route candidate 106 having been unregistered, the route extracting function 14c registers this as a first support route. The route name at this time is named based on a branch name which this route passes through.

Figure 13:
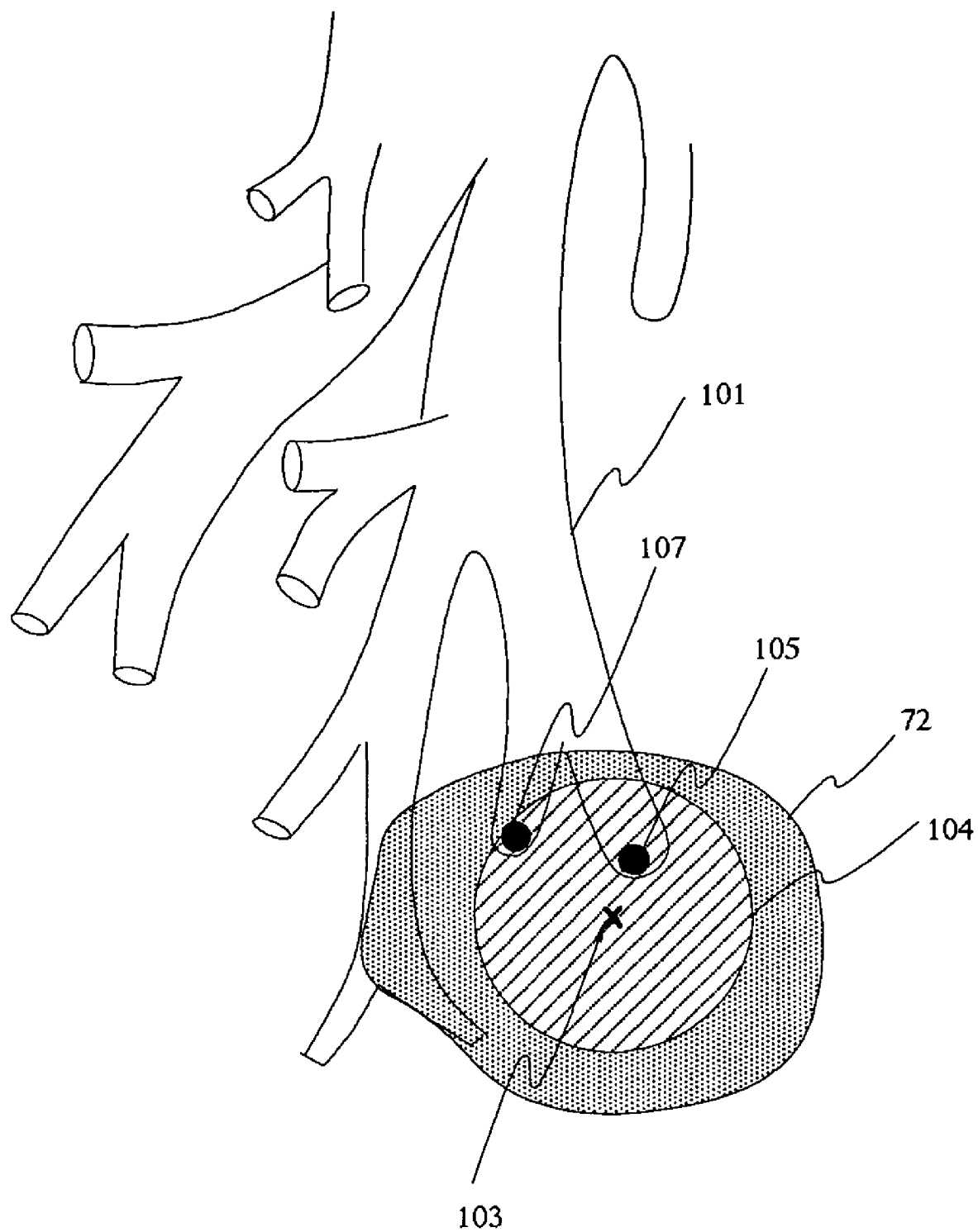
FIG. 13 is a third diagram describing the processing in FIG. 9.
Figure 14:
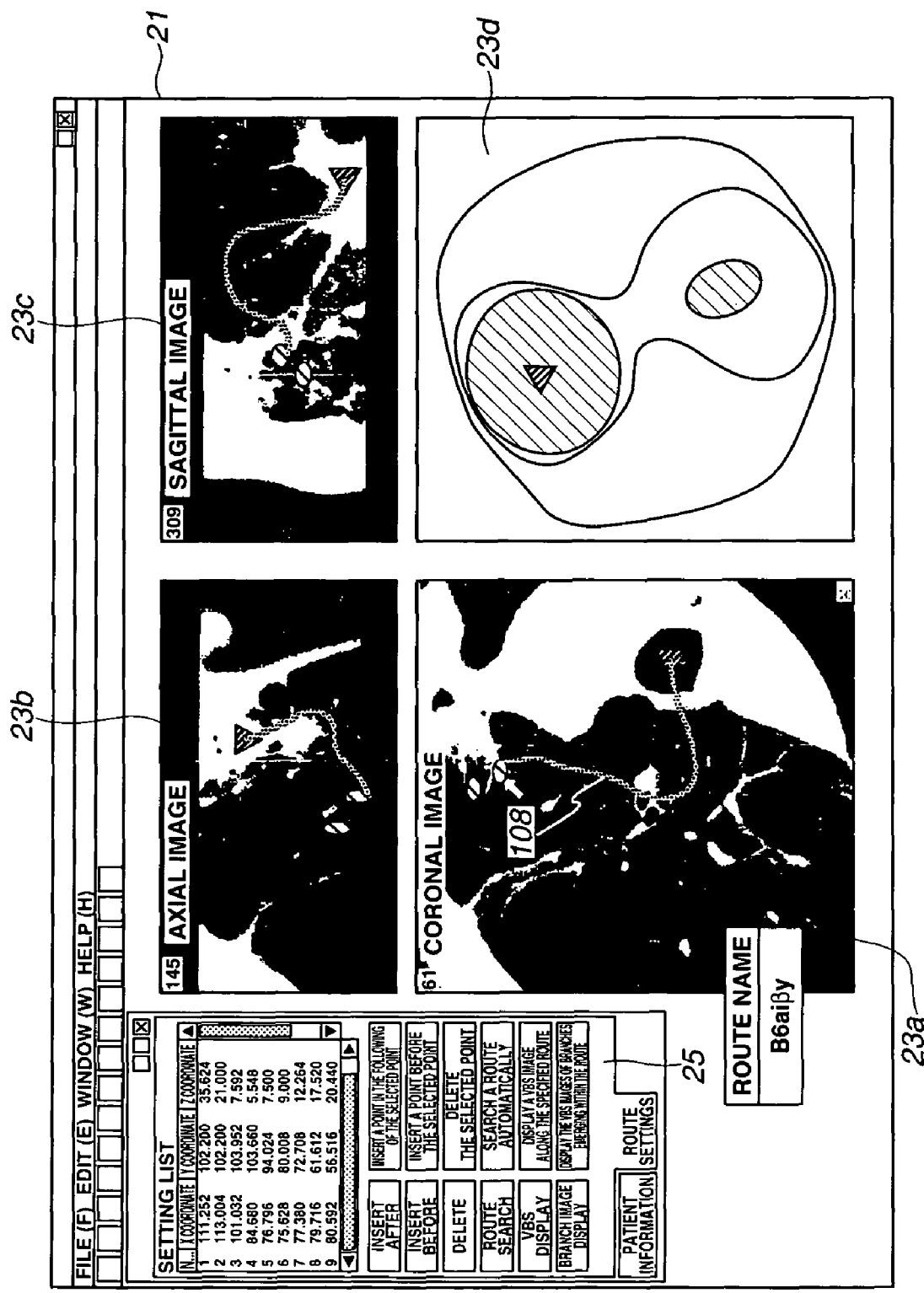
FIG. 14 is a second diagram illustrating the route setting screen to be developed in the processing in FIG. 9.

Upon the first support route being determined, as shown in FIG. 13, the route extracting function 14c increases the radius of the search area 104 centered on the center of gravity 103 to enlarge the search area 104, and takes the point where the bronchial tube is positioned next within the search area 104 as an end point 107. Subsequently, the route extracting function 14c determines a second route candidate 108 connecting the starting point 71 and this end point 107 as shown in FIG. 14. In the event of this second route candidate 108 having been unregistered, the route extracting function 14c registers this as a second support route. In FIG. 14, the second route candidate 108 is different from the first support route in FIG. 12, so the second route candidate 108 becomes the second support route. The route name at this time is also named based on a branch name which this route passes through.

Figure 15:
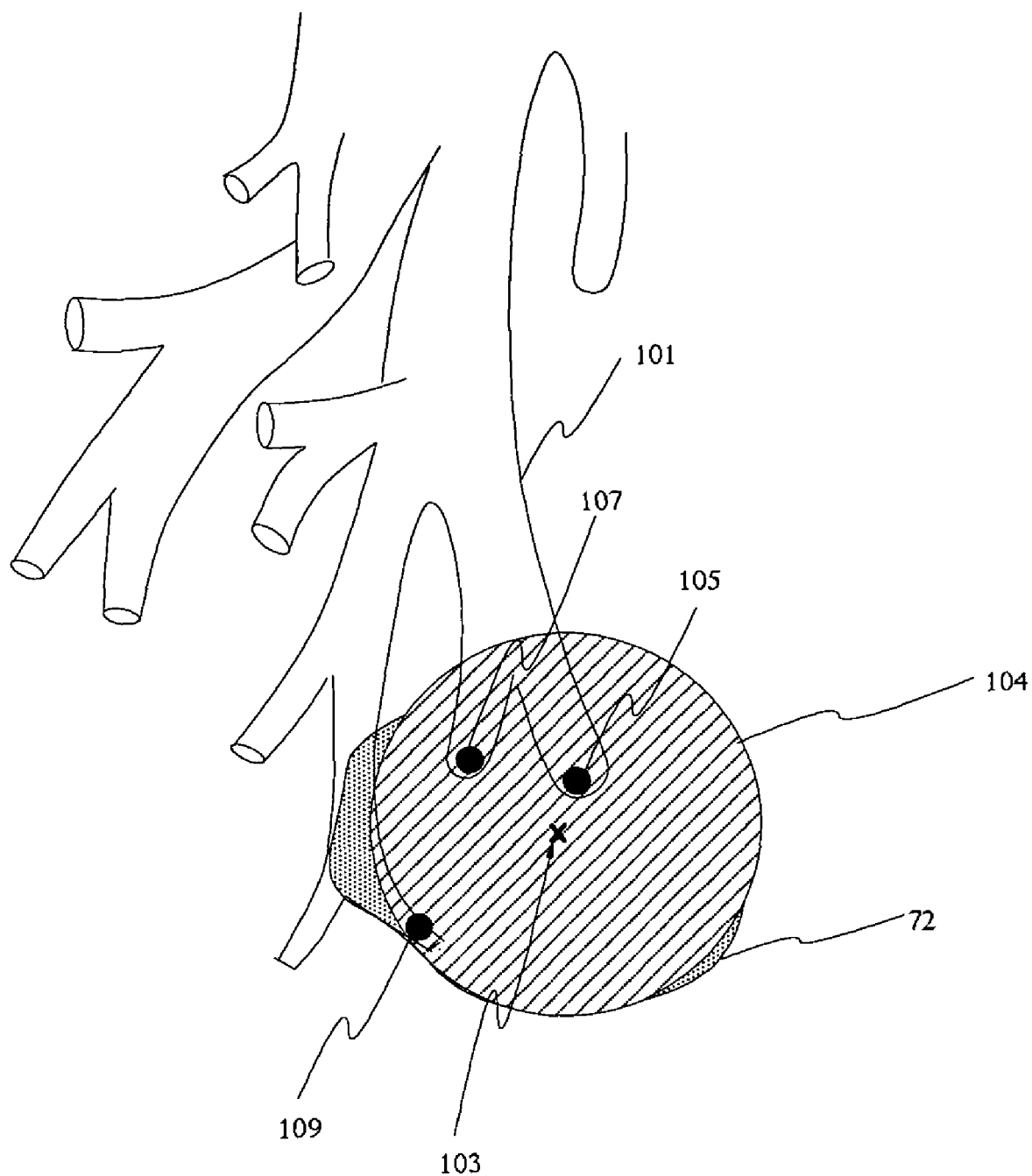
FIG. 15 is a fourth diagram describing the processing in FIG. 9.
Figure 16:
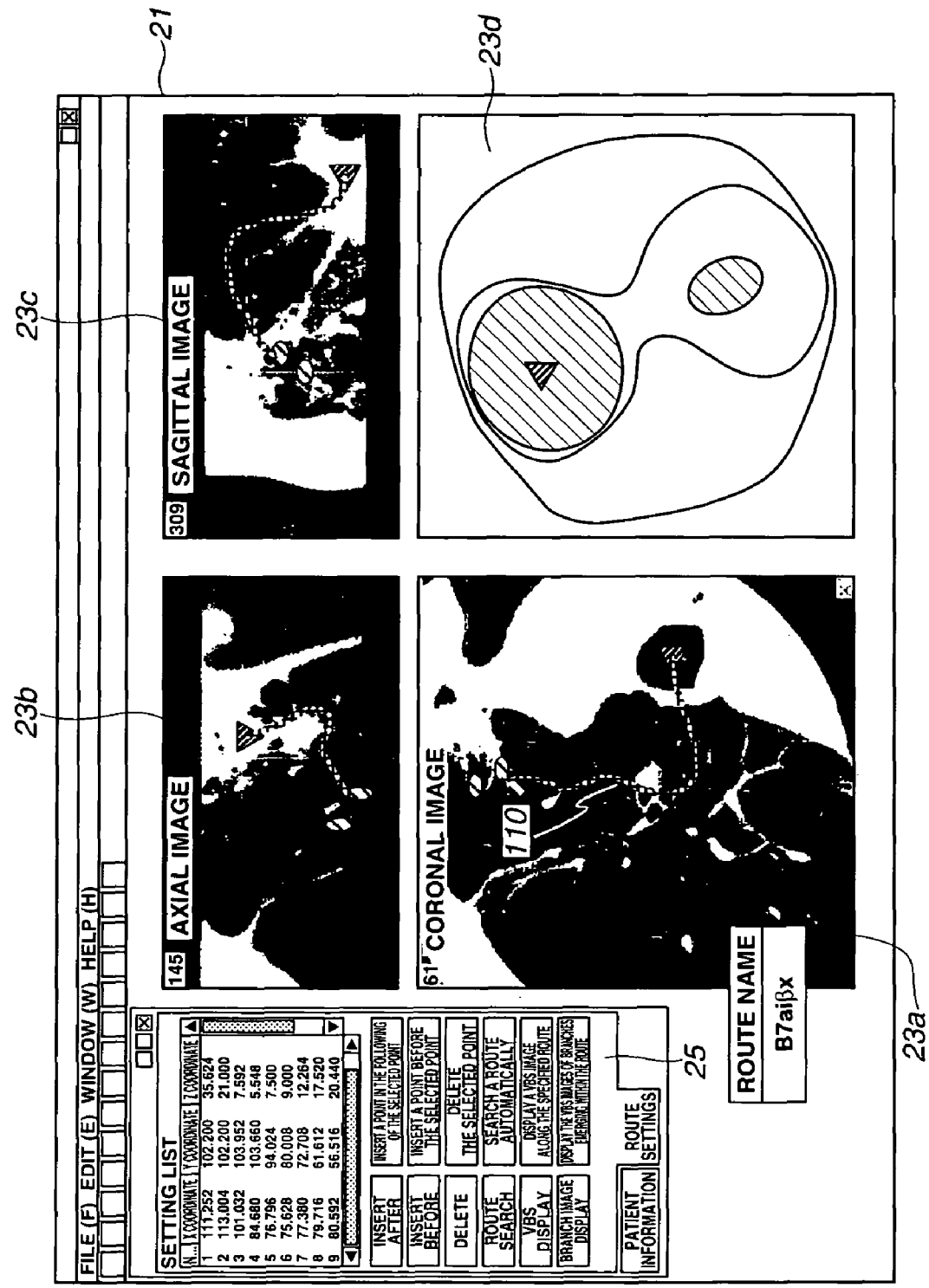
FIG. 16 is a third diagram illustrating the route setting screen to be developed in the processing in FIG. 9.

With the present embodiment, the number of routes is three, so in the same way, upon the second support route being determined, as shown in FIG. 15, the route extracting function 14c further increases the radius of the search area 104 centered on the center of gravity 103 to enlarge the search area 104, and takes the point where the bronchial tube is positioned next within the search area 104 as an end point 109, and determines a third route candidate 110 connecting the starting point 71 and this end point 109 as shown in FIG. 16. In the event of this third route candidate 110 having been unregistered, the route extracting function 14c registers this as a third support route. In FIG. 16, the third route candidate 110 is different from the first and second support routes, so the third candidate 110 becomes the third support route. The route name at this time is also named based on a branch name which this route passes through.

Thus, the same number of support routes as the specified number of routes can be set. All of the biopsy areas 72 are subjected to the above processing, thereby setting the same number of support routes as the number of routes specified for each of the biopsy areas 72.

Next, of the multiple support routes having been set, description will be made regarding selection of the most appropriate support route using the route verifying function 14d of the route setting unit 14.

Figure 17:
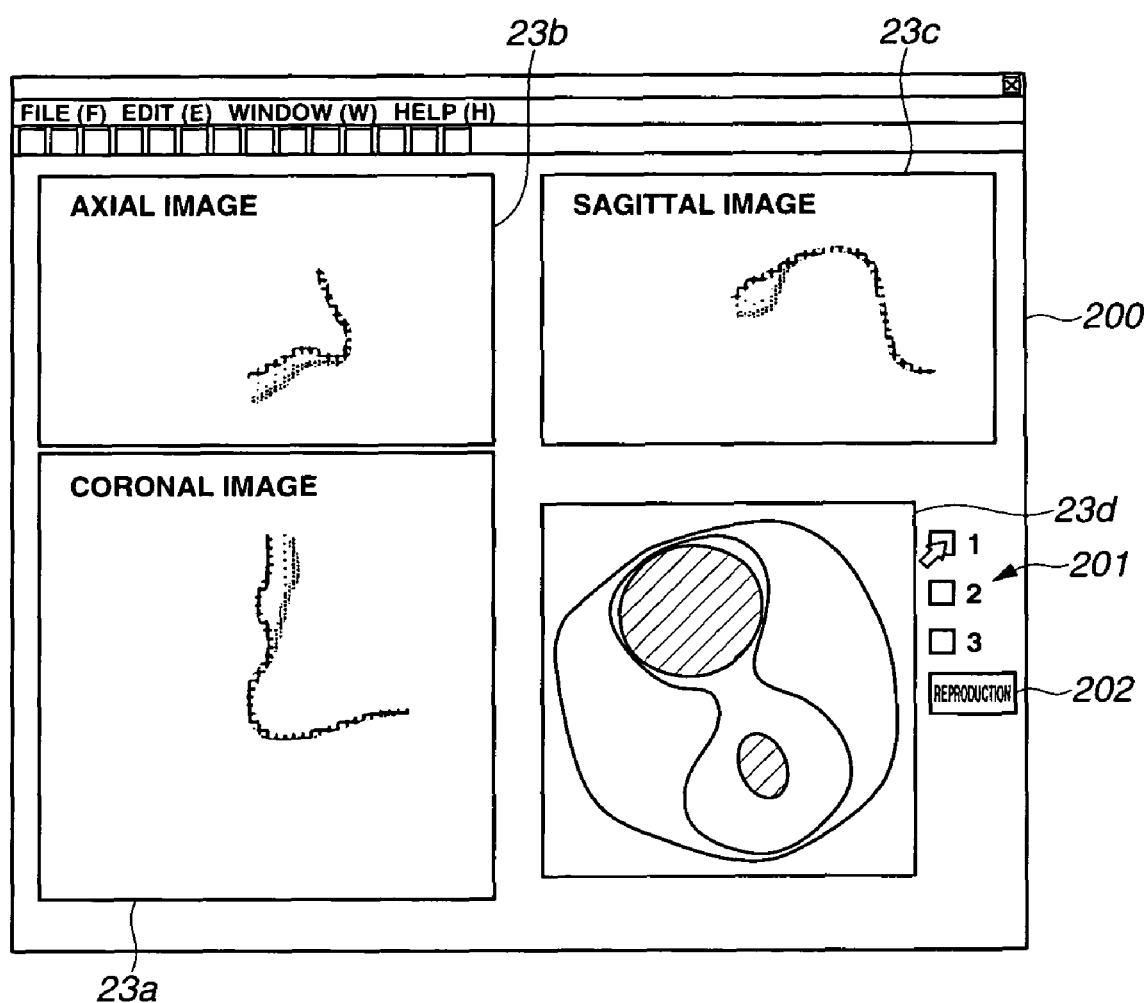
FIG. 17 is a diagram illustrating a route verification window using an MPR image generated by the route verifying function of the route setting unit in FIG. 2.

Upon a verification start signal being input from the input device 19, the route verifying function 14d of the route setting unit 14 displays a route verification window 200 such as shown in FIG. 17 on the monitor 6. The route verification window 200 has a coronal image 23a, an axial image 23b, a sagittal image 23c, serving as MPR images, a VBS image display area 23d for displaying a VBS image, checkboxes 201 for specifying the multiple support routes set, and a reproduction button 202 for reproducing the VBS image to be displayed on the VBS image display area 23d as a moving image along a support route. On the coronal image 23a, axial image 23b, and sagittal image 23c of this route verification window 200, the multiple support routes which have been set are displayed, and in the case of FIG. 17, three support routes are displayed.

Figure 18:
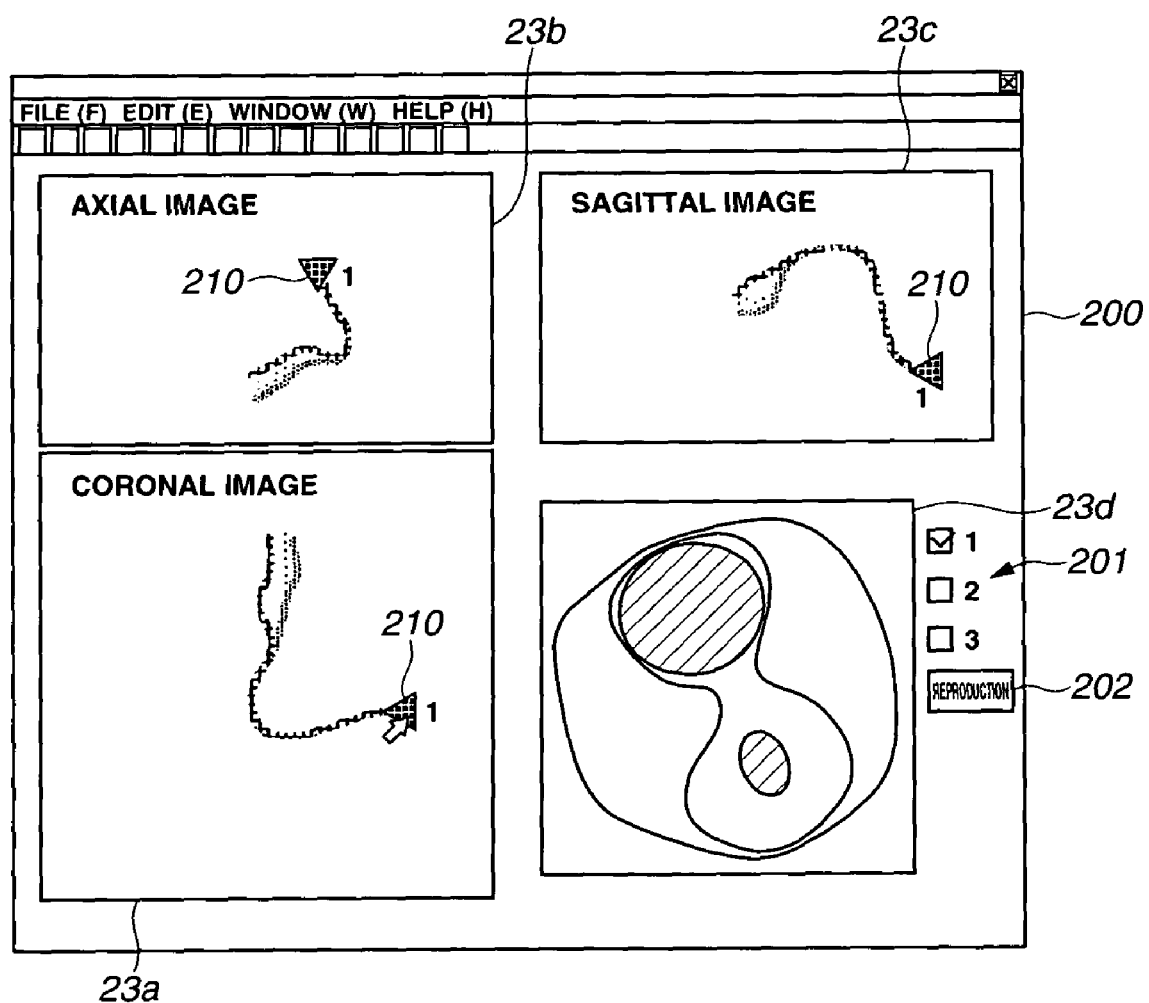
FIG. 18 is a first diagram describing operation of the route verification window in FIG. 17.

Upon the user selecting the first support route of the three support routes at the checkboxes 201 by operating the input device 19 for example, as shown in FIG. 18, the route verifying function 14d displays a pointer 210 on the starting-point position of the first support route on the coronal image 23a, axial image 23b, and sagittal image 23c, and also displays the VBS image of the first support route position where this pointer 210 is positioned on the VBS image display area 23d. Note that the pointer 210 is capable of moving on the first support route alone, and character data "1" indicating that this pointer is the pointer of the first support route is also displayed near the pointer 210.

Figure 19:
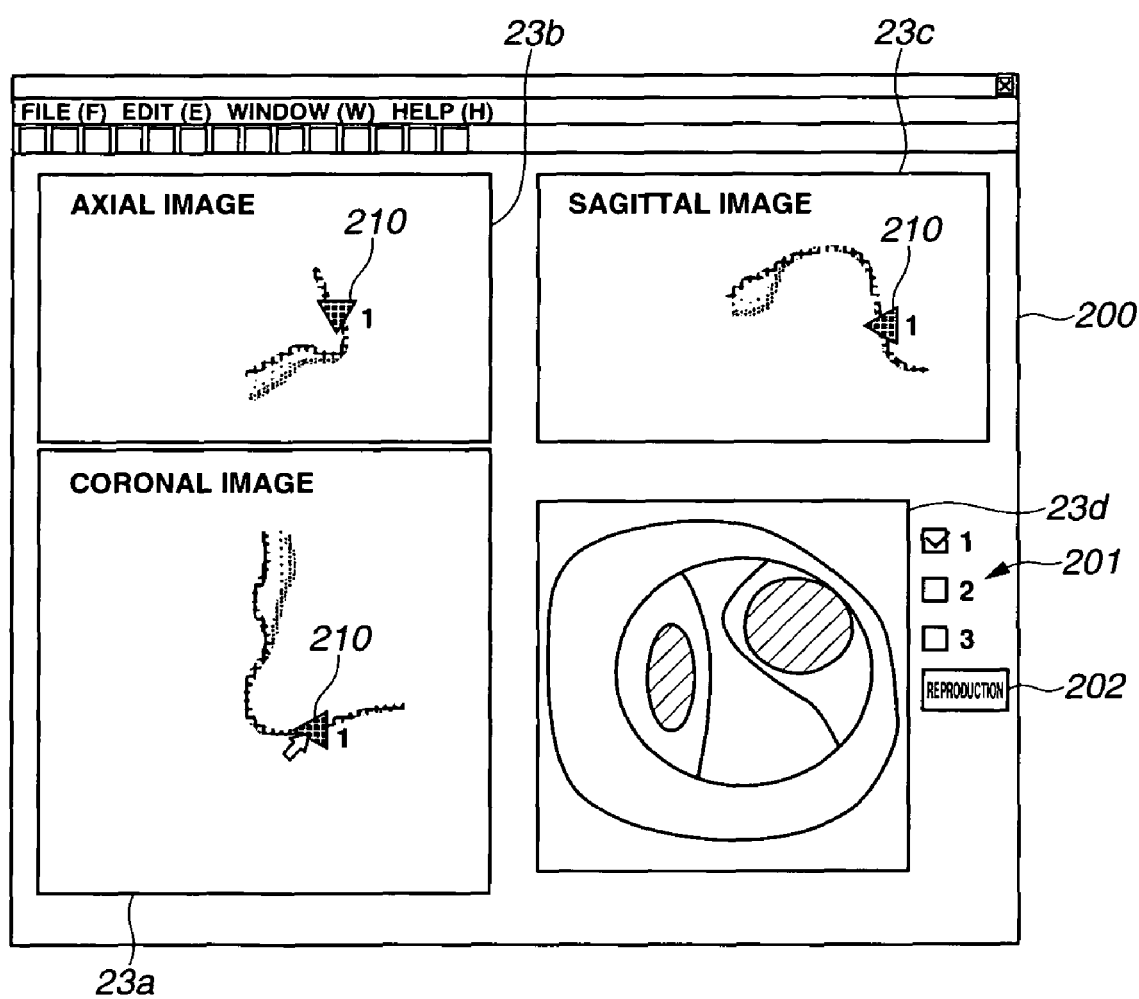
FIG. 19 is a second diagram describing operation of the route verification window in FIG. 17.

Upon the user moving the pointer 210 toward an arbitrary position on the coronal image 23a along the first support route by operating the input device 19 for example, as shown in FIG. 19, the route verifying function 14d changes the VBS image to be displayed on the VBS image display area 23d to the VBS image at the position where the moved pointer 210 is positioned on the position of the first support route. Note that transition is made from the VBS image in FIG. 18 to the VBS image in FIG. 19, as a moving image of the VBS image corresponding to moving of the pointer 210.

Figure 20:
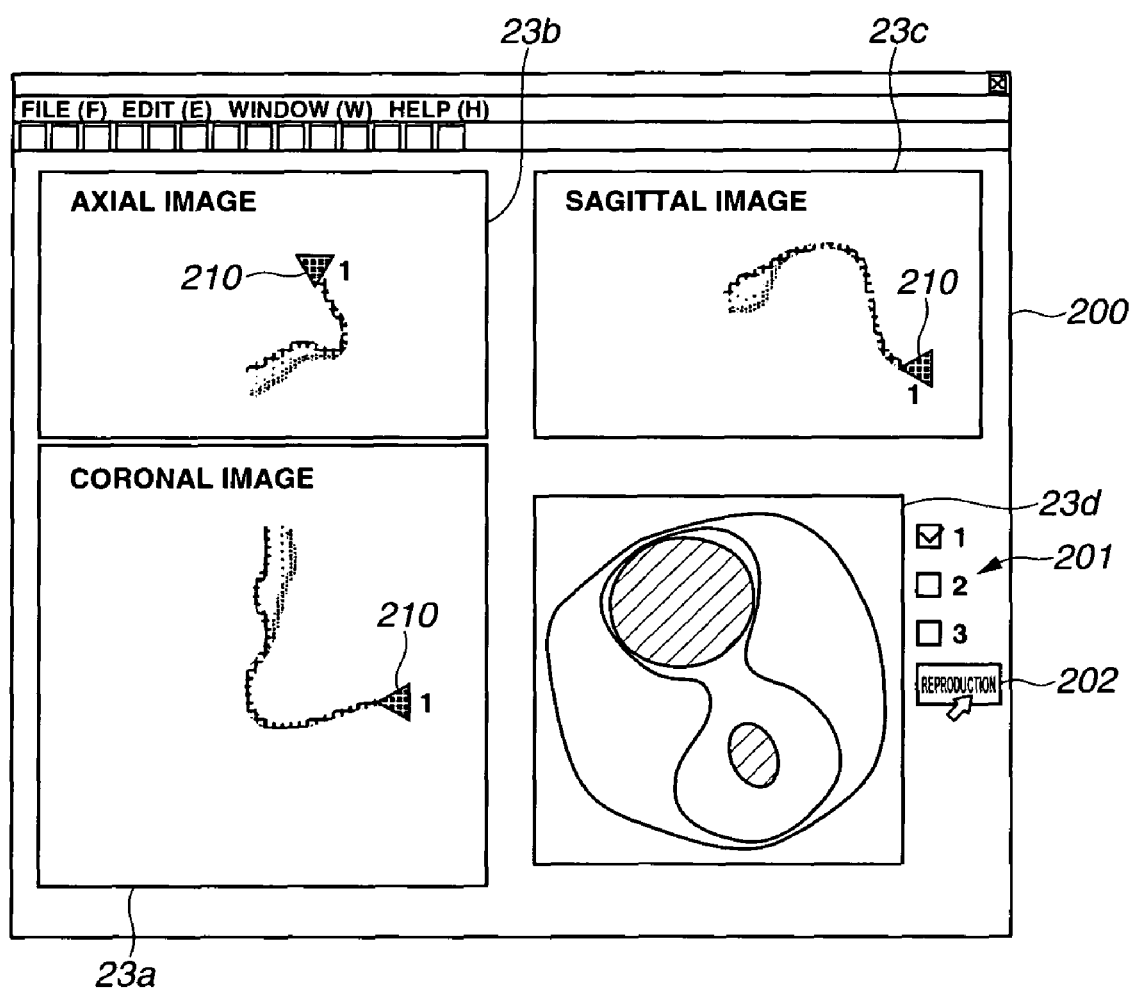
FIG. 20 is a third diagram describing operation of the route verification window in FIG. 17.
Figure 21:
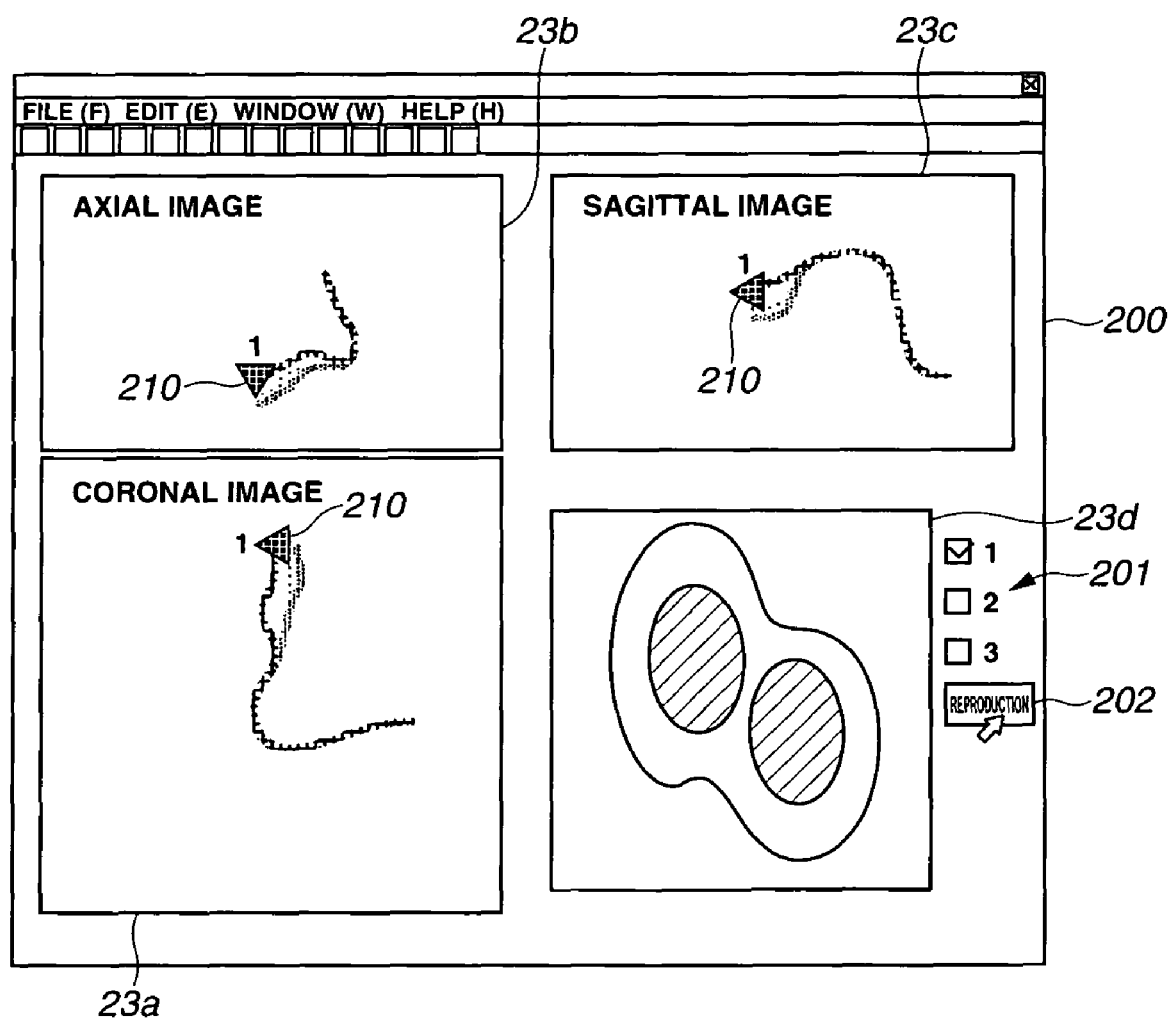
FIG. 21 is a fourth diagram describing operation of the route verification window in FIG. 17.

Also, as shown in FIG. 20 for example, upon the user clicking the reproduction button 202 using the input device 19 in a state wherein the pointer 210 is pointed at the starting-point position of the first support route, the route verifying function 14d moves the pointer 210 from the starting-point position to the end-point position along the support route, while displaying the VBS image on the VBS image display area 23d as a moving image, and finally the route verifying function 14d makes the VBS image to be displayed on the VBS image display area 23d into the VBS image at the end-point position as shown in FIG. 21.

Note that in the event that the pointer 210 is pointed at an arbitrary position of the first support route, upon the user clicking the reproduction button 202, the route verifying function 14d moves the pointer 210 from that position to the end-point position along the support route, while displaying the VBS image on the VBS image display area 23d as a moving image, and finally the route verifying function 14d makes the VBS image, to be displayed on the VBS image display area 23d, as the VBS image at the end-point position as shown in FIG. 21.

Thus, the user can confirm the VBS images on the first support route, so that verification can be made regarding whether or not the first support route is a suitable route.

Applying these processes to the second support route and the third support route enables the most appropriate route to be verified and selected.

Figure 22:
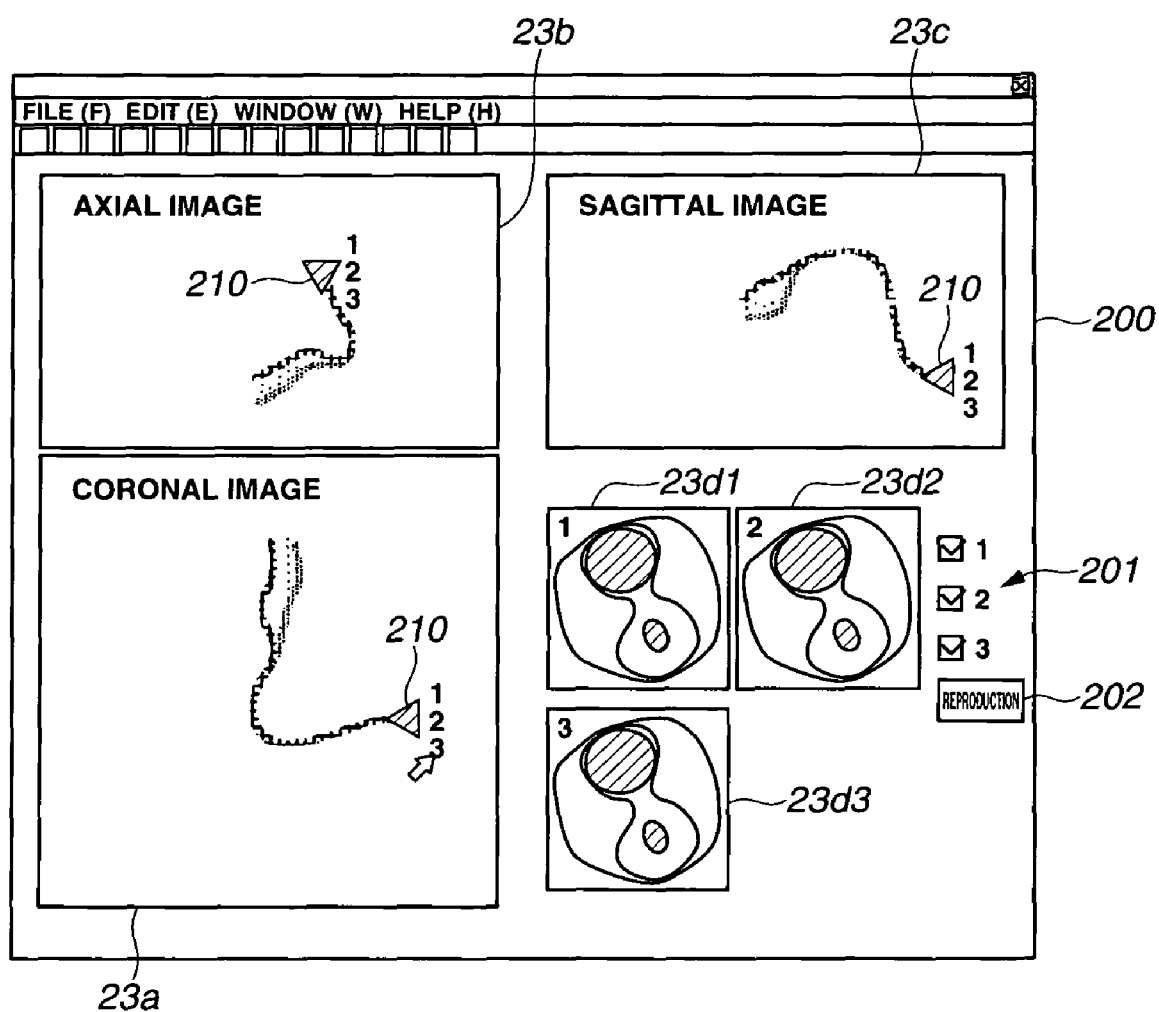
FIG. 22 is a fifth diagram describing operation of the route verification window in FIG. 17.

Also, with the route verification window 200, multiple support routes can be verified simultaneously. That is to say, as shown in FIG. 22, for example, upon the user checking all of the three support routes at the checkboxes 201, the pointer 210 is pointed at the starting-point position of the support routes on the coronal image 23a, axial image 23b, and sagittal image 23c, but the starting-point positions of the three support routes are the same, so the number of the pointers 210 to be displayed is only one. At this time, however, character data "1", "2", and "3" which indicate the first through third support route pointers are also displayed near the pointer 210.

Also, with the route verification window 200 in FIG. 22, three of a VBS image display area 23d1, VBS image display area 23d2, and VBS image display area 23d3 are provided for displaying the VBS image of each route instead of the VBS image display area 23d. On the VBS image display area 23d1, VBS image display area 23d2, and VBS image display area 23d3, the VBS image at the position where the pointer 210 is positioned on each route is displayed. In FIG. 22, the pointer 210 on each route is positioned at the starting-point position, so the VBS images to be displayed on the first-insertion-route VBS image display area 23d1, the second-insertion-route VBS image display area 23d2, and the third-insertion-route VBS image display area 23d3 are the same, and the VBS image at the starting-point position is displayed.

Figure 23:
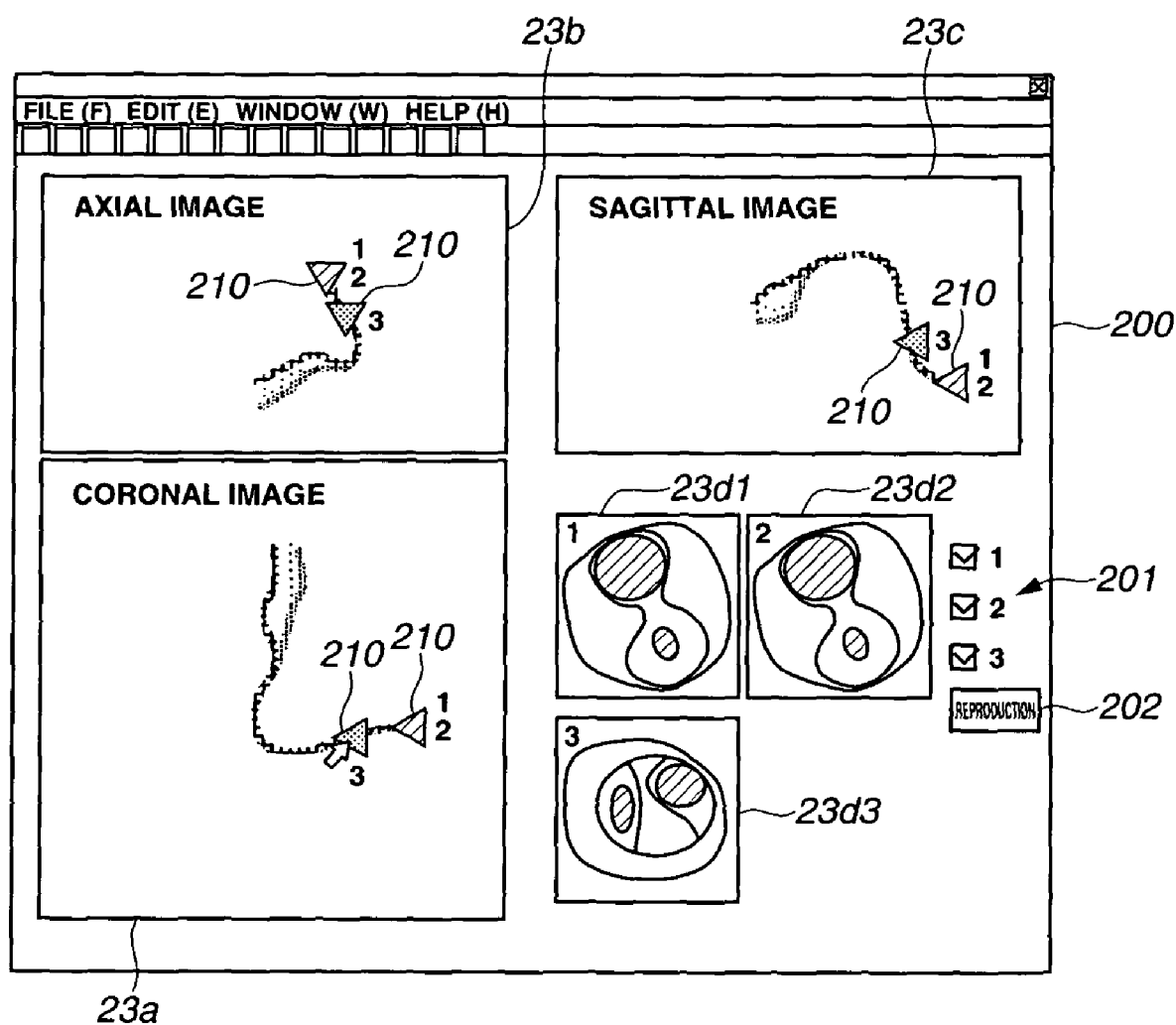
FIG. 23 is a sixth diagram describing operation of the route verification window in FIG. 17.

Subsequently, in this state, upon the user clicking the character data "3" near the pointer 210 for example, and moving the pointer 210 along the third insertion route using the route verifying function 14d, as shown in FIG. 23, the third insertion route pointer 210 is pointed on the third insertion route, and also the VBS image where the third insertion route pointer 210 is positioned is displayed on the VBS image display area 23d3. At this time, on the VBS image display area 23d1, and the VBS image display area 23d2 the VBS image at the starting-point position is displayed without any change.

These character-data clicking operations are enabled on each insertion route, and performing such an operation on an insertion route displays the VBS image where the corresponding insertion route pointer 210 is positioned on the VBS image display area corresponding to the insertion route where the operation is performed. As described above, the VBS image changes as a moving image as the pointer 210 moves.

Figure 24:
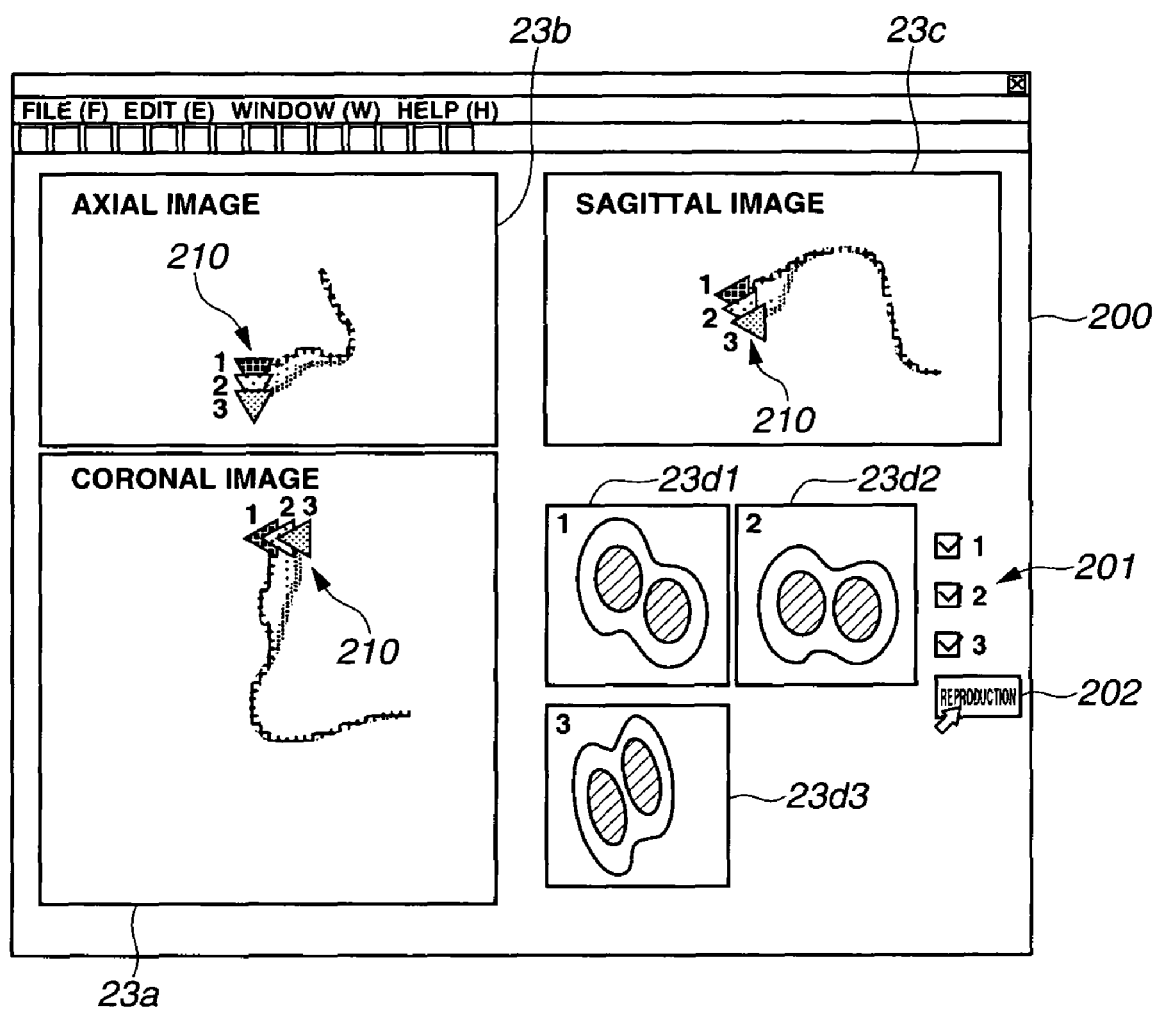
FIG. 24 is a seventh diagram describing operation of the route verification window in FIG. 17.

Also, as shown in FIG. 24, upon the user clicking the reproduction button 202, the respective pointers 210 are moved along all of the insertion routes by the route verifying function 14d, while displaying the VBS images as a moving image on the first-insertion-route VBS image display area 23d1, second-insertion-route VBS image display area 23d2, and third-insertion-route VBS image display area 23d3, and finally the route verifying function 14d makes the VBS images to be displayed on the first-insertion-route VBS image display area 23d1, second-insertion-route VBS image display area 23d2, and third-insertion-route VBS image display area 23d3 into the VBS image at the end-point position, as shown in FIG. 21.

Figure 25:
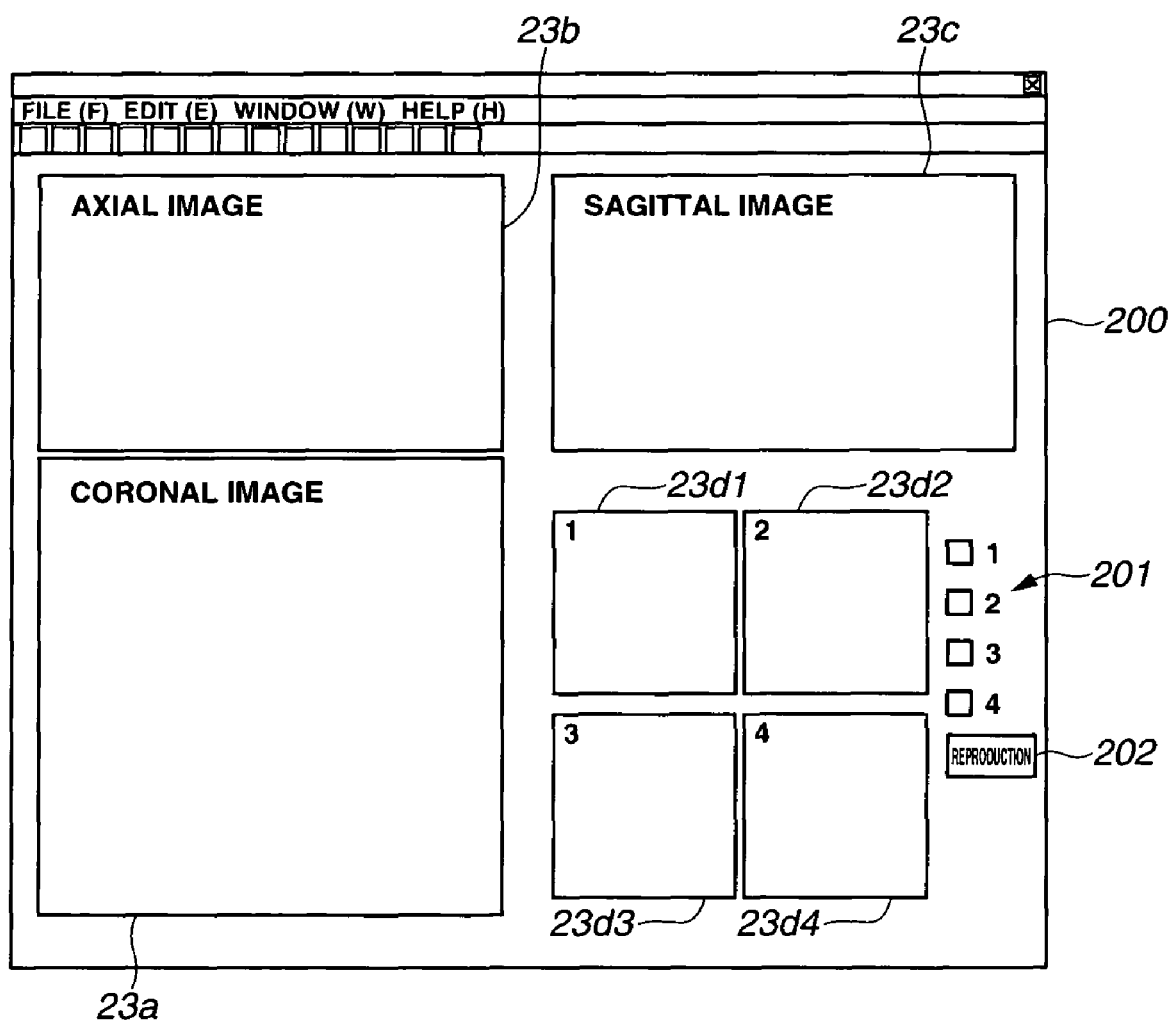
FIG. 25 is an eighth diagram describing operation of the route verification window in FIG. 17.

As shown in FIG. 25, in the event of four insertion routes, a fourth-insertion-route VBS image display area 23d4 is displayed, but the actions at that time are the same as those in FIG. 22 through FIG. 24.

Figure 26:
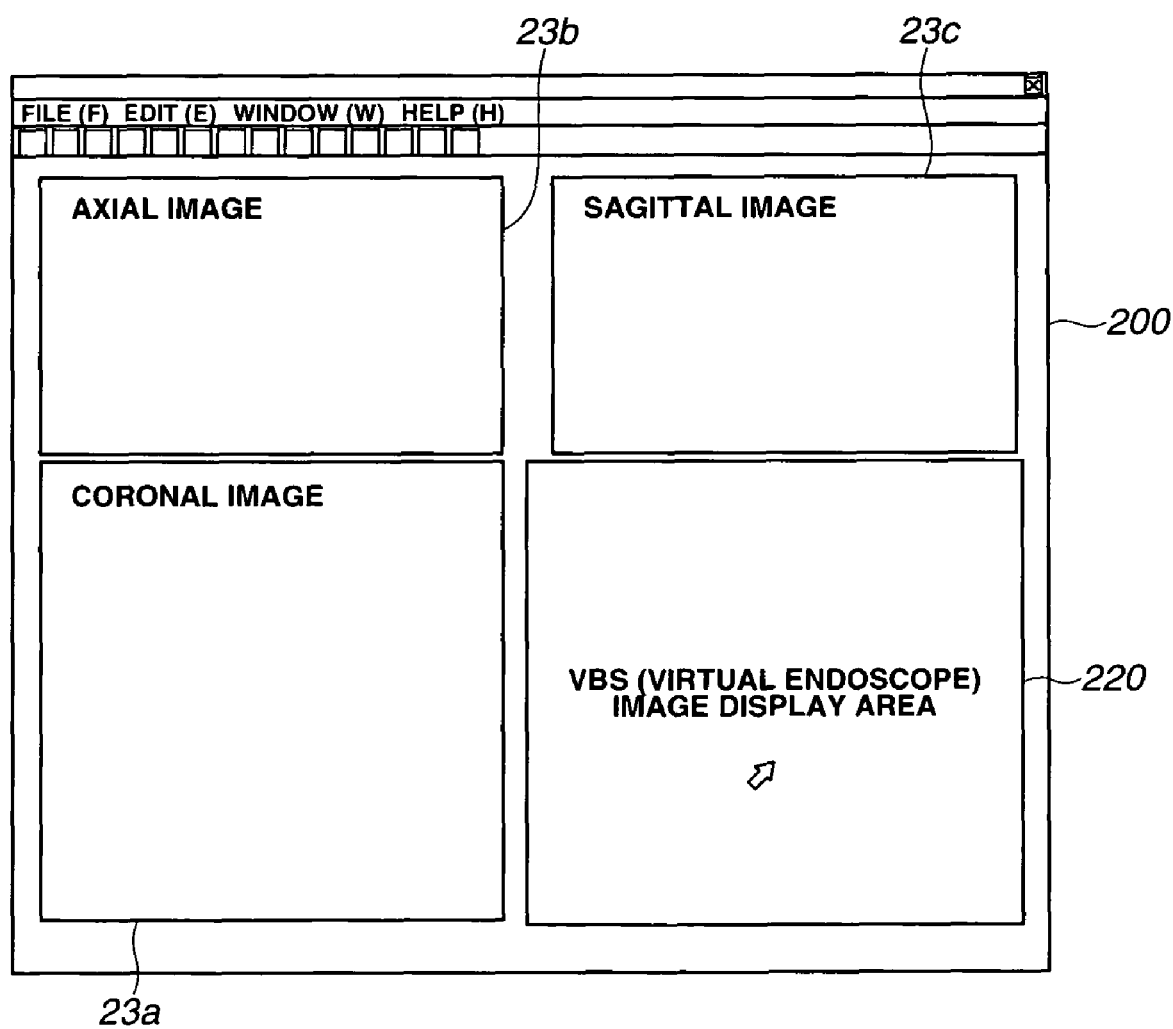
FIG. 26 is a ninth diagram describing operation of the route verification window in FIG. 17.

Also, in the event of five insertion routes or more, when displaying the VBS images simultaneously, the VBS images are displayed too much small, so as shown in FIG. 26, a VBS display frame 220 is displayed in the route verification window 200.

Figure 27:
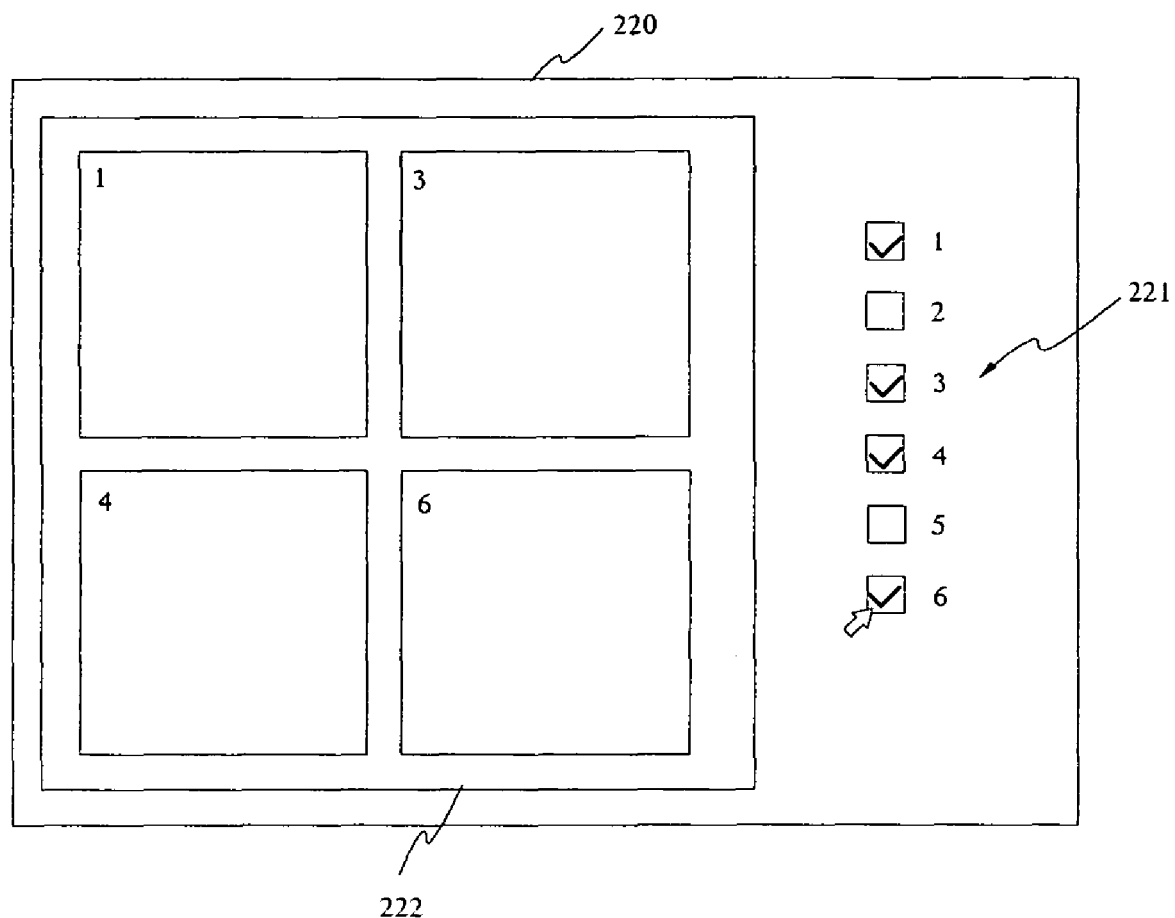
FIG. 27 is a first diagram describing the VBS display frame in FIG. 26.

As shown in FIG. 27, this VBS display frame 220 has checkboxes 221 for specifying an arbitrary support route within six support routes for example, and a VBS image display portion 222 made up of VBS image display areas for displaying VBS images in the case in which the support routes selected at the checkboxes 221 are four or less. For example, upon the user selecting the first support route, third support route, fourth support route, and sixth support route at the checkboxes 221, on the upper left of each VBS image display area of the VBS image display portion 222 the number of the corresponding support route is displayed, and on each VBS image display area the VBS image where the pointer 210 on each support route is positioned is displayed. The display method of VBS images is the same as that in FIG. 22 through FIG. 24.

Figure 28:
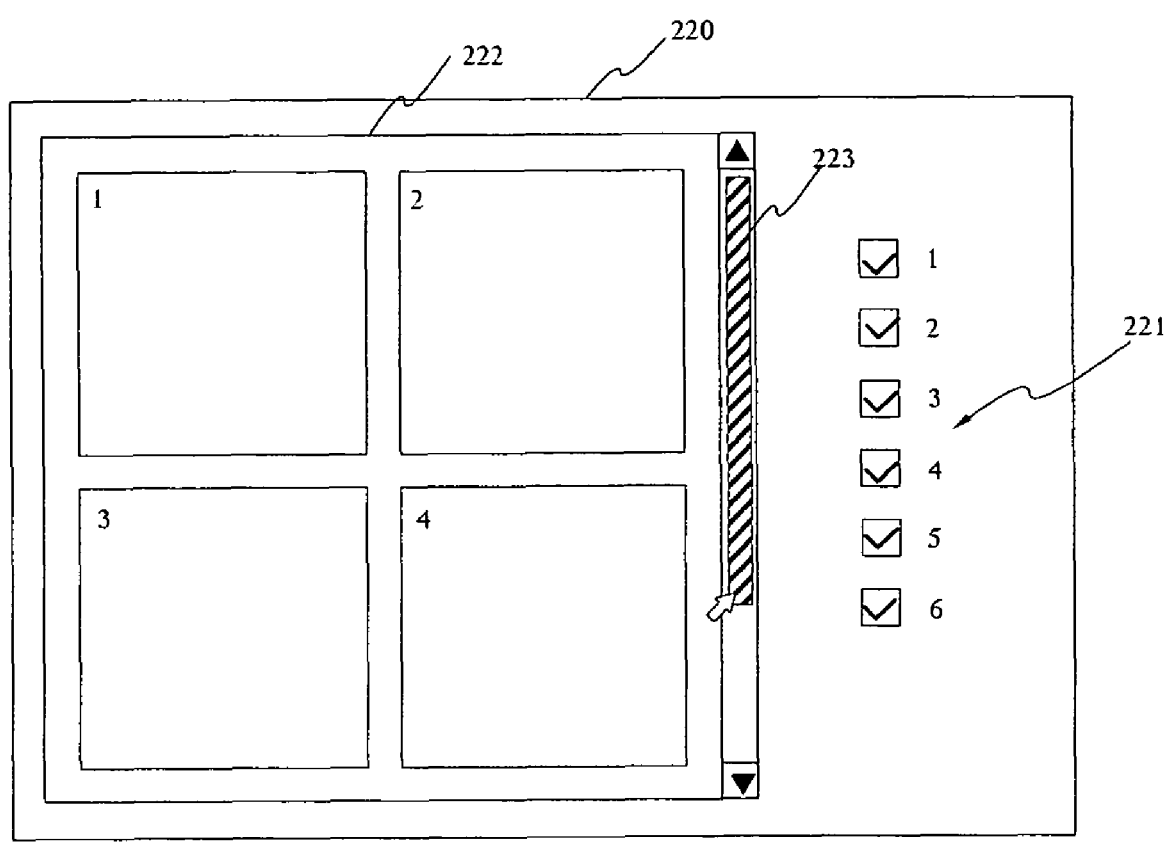
FIG. 28 is a second diagram describing the VBS display frame in FIG. 26.
Figure 29:
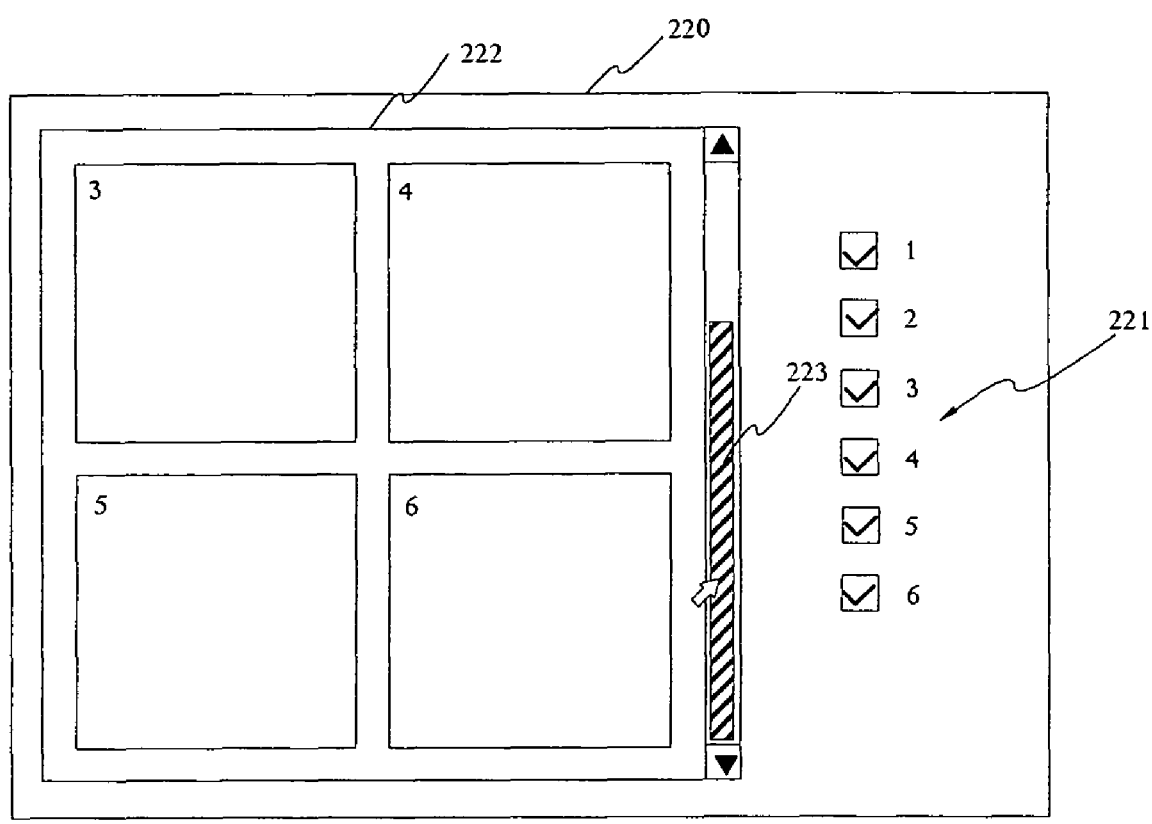
FIG. 29 is a third diagram describing the VBS display frame in FIG. 26.

Also, upon the user selecting all of the six support routes at the checkboxes 221, as shown in FIG. 28 and FIG. 29, for example, a scroll bar 223 is displayed on the VBS image display portion 222. The number of the VBS image display areas to be displayed on the VBS image display portion 222 is restricted to four, but the VBS images of the six VBS image display areas can be confirmed sequentially by operating the scroll bar 223. FIG. 28 illustrates a state in which the VBS images on the first through fourth insertion routes can be displayed, and FIG. 29 illustrates a state in which the VBS images on the third through sixth insertion routes can be displayed.

Figure 30:
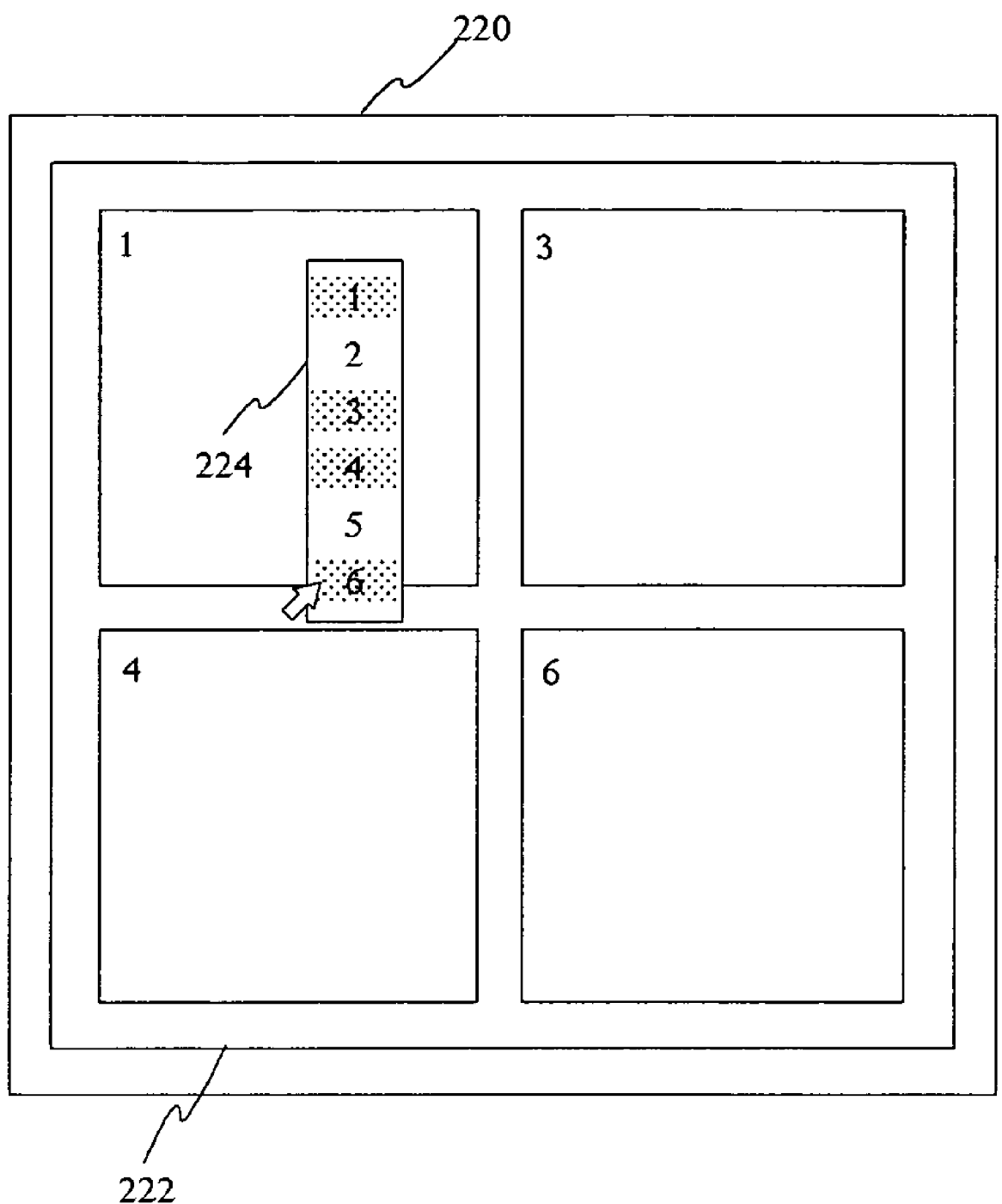
FIG. 30 is a diagram describing a modification of the VBS display frame in FIG. 26.

Note that instead of the checkboxes 221, an arrangement may be made wherein, as shown in FIG. 30, upon the user operating the input device 19, a pop-up window 224 is displayed on the VBS display frame 220, and the user can select an insertion route on the pop-up window 224, and in this case, restricting the number of selections to four or less enables the display size of the VBS images to be set to a confirmable size.

Figure 31:
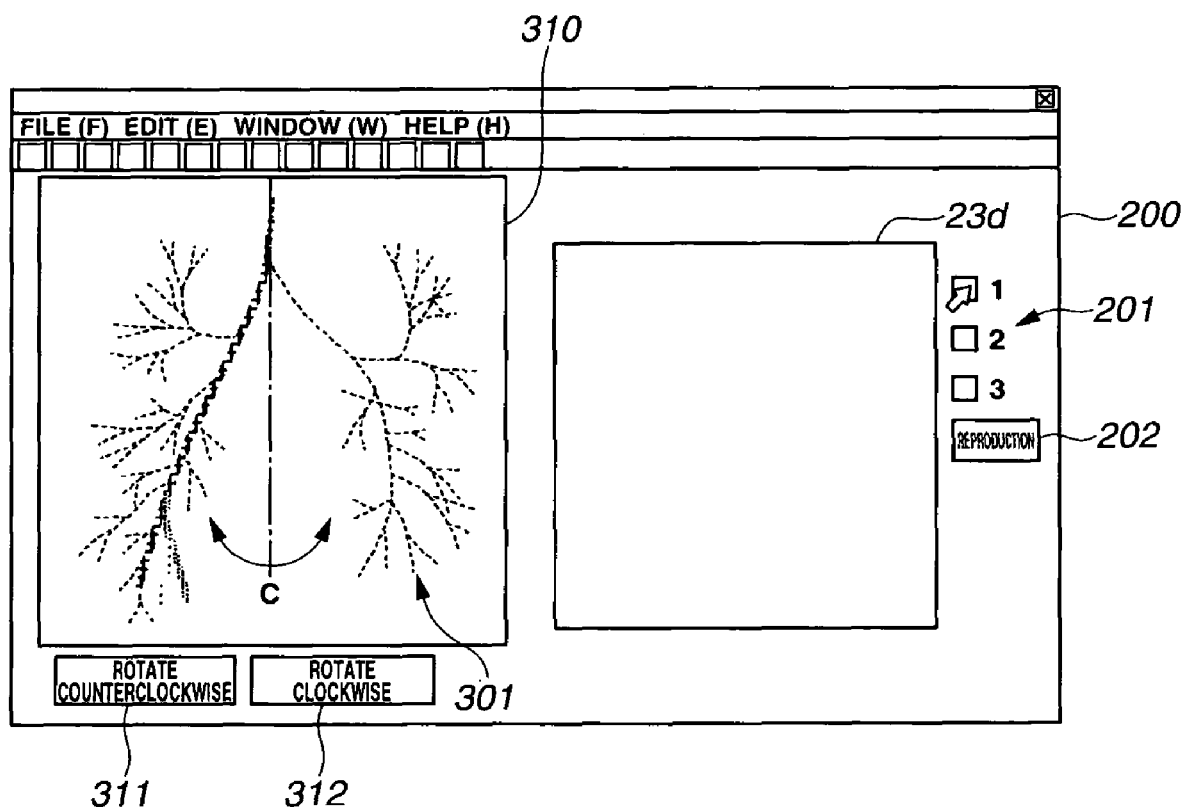
FIG. 31 is a diagram illustrating the route verification window using a thinning model image generated by the route verifying function of the route setting unit in FIG. 2.

Also, upon the user inputting a route display modifying signal from the input device 19, the route verifying function 14d of the route setting unit 14 according to the present embodiment displays a route verification window 200 such as shown in FIG. 31 on the monitor 6.

Figure 32:
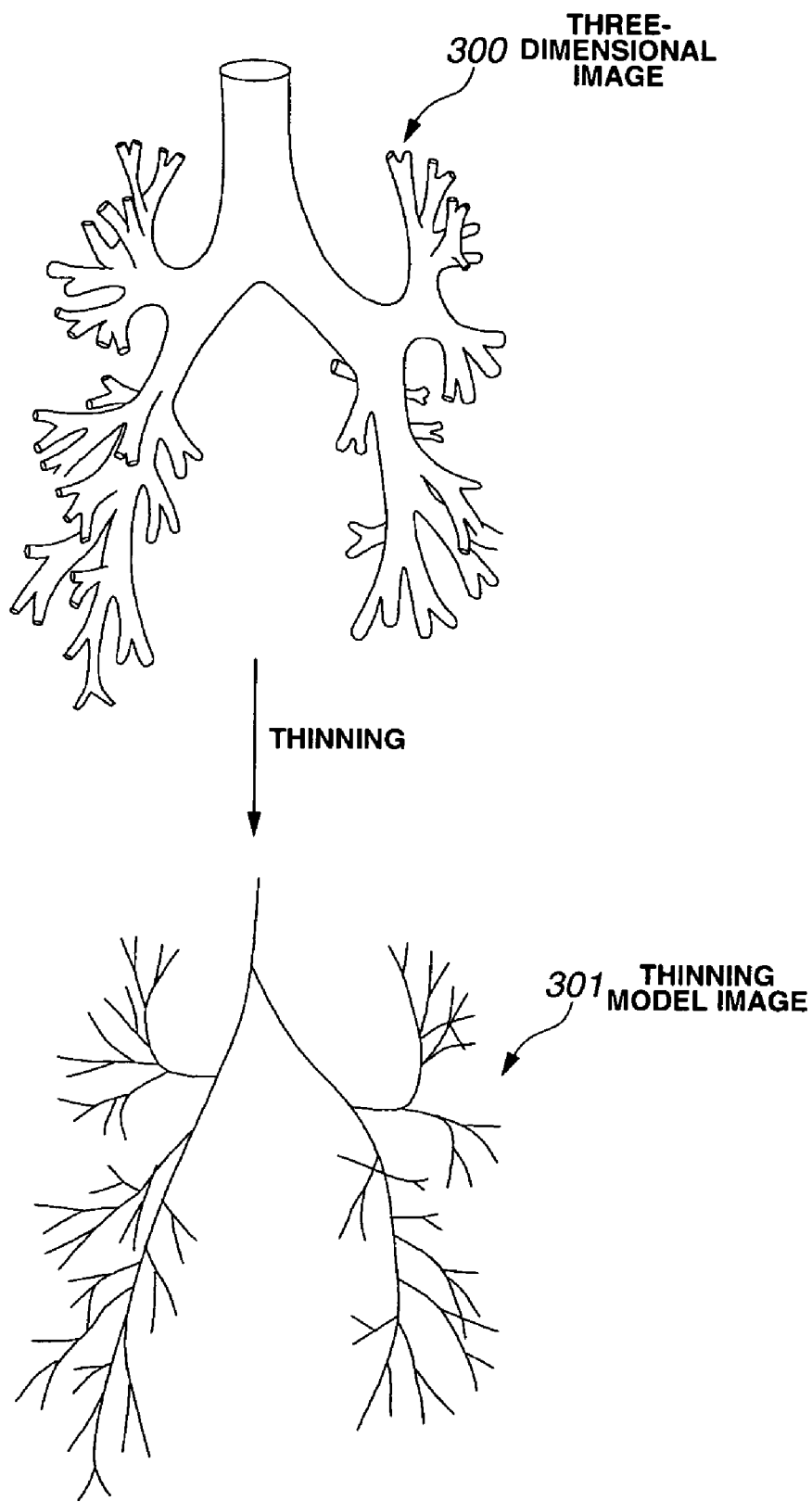
FIG. 32 is a diagram describing the thinning model image in FIG. 31.

The route verifying function 14d generates a bronchial tube thinning model image 301 by thinning a bronchial tube three-dimensional image 300 based on CT image data such as shown in FIG. 32, and the route verification window 200 can display the thinning model image 301 on a three-dimensional image display area 310 instead of the coronal image 23a, axial image 23b, and sagittal image 23c, shown in FIG. 31.

A rotate-counterclockwise button 311 and a rotate-clockwise button 312 for rotating the thinning model image 301 around the C axis are provided underneath this three-dimensional image display area 310, and the others are the same as FIG. 17.

Figure 33:
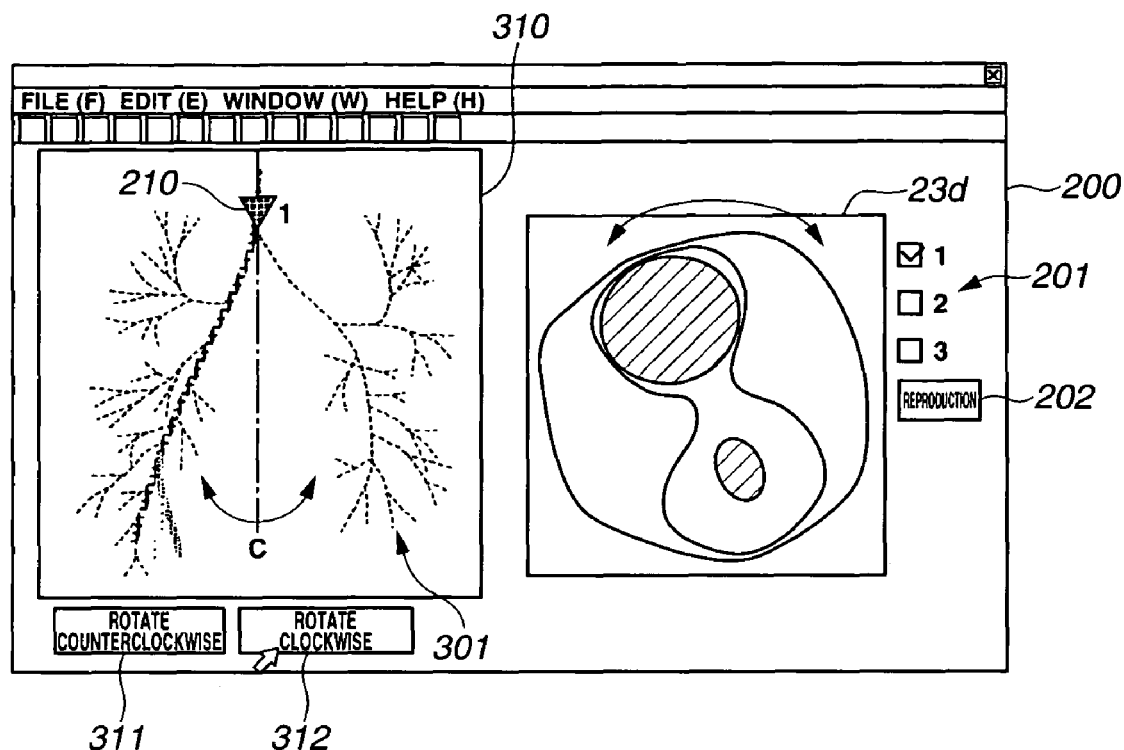
FIG. 33 is a first diagram describing operation of the route verification window in FIG. 31.

As shown in FIG. 33, upon the user selecting the first insertion route at the checkboxes 201 for example, the pointer 210 is pointed at the starting-point position on the thinning model image 301, and the VBS image of the first insertion route at the starting-point position is displayed on the VBS image display area 23d.

At this time, upon the user clicking the rotate-counterclockwise button 311 or rotate-clockwise button 312, the thinning model image 301 rotates counterclockwise or clockwise around the C axis for the period corresponding to clicking. The VBS image on the VBS image display area 23d is an image from the fixed starting-point, so upon the thinning model image 301 rotating around the C axis, the VBS image rotates in sync with rotation thereof. Thus, the VBS image can be confirmed by arbitrarily rotating the VBS image within the bronchial tube.

Figure 34:
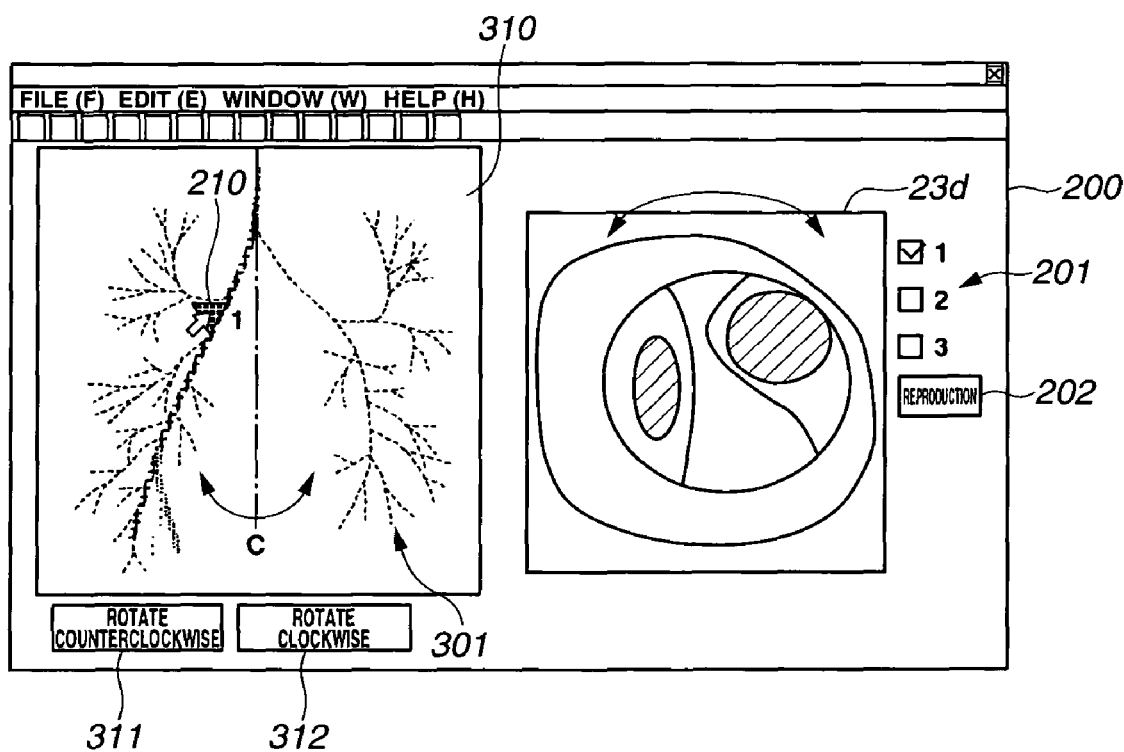
FIG. 34 is a second diagram describing operation of the route verification window in FIG. 31.

Also, as shown in FIG. 34, the pointer 210 on the thinning model image 301 can be moved to the position on an arbitrary insertion route, and in this case, as described above, while the VBS image is changing as a movie image, the VBS image of the insertion route where the pointer 210 is positioned is displayed on the VBS image display area 23d.

Figure 35:
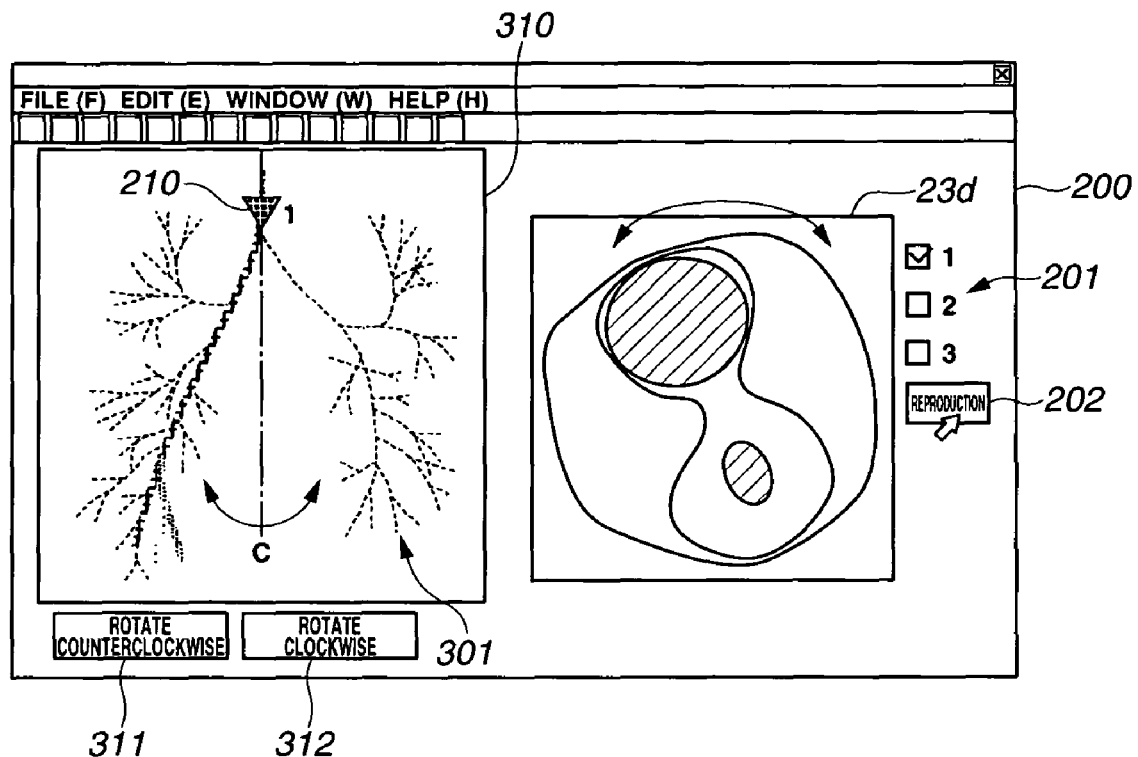
FIG. 35 is a third diagram describing operation of the route verification window in FIG. 31.
Figure 36:
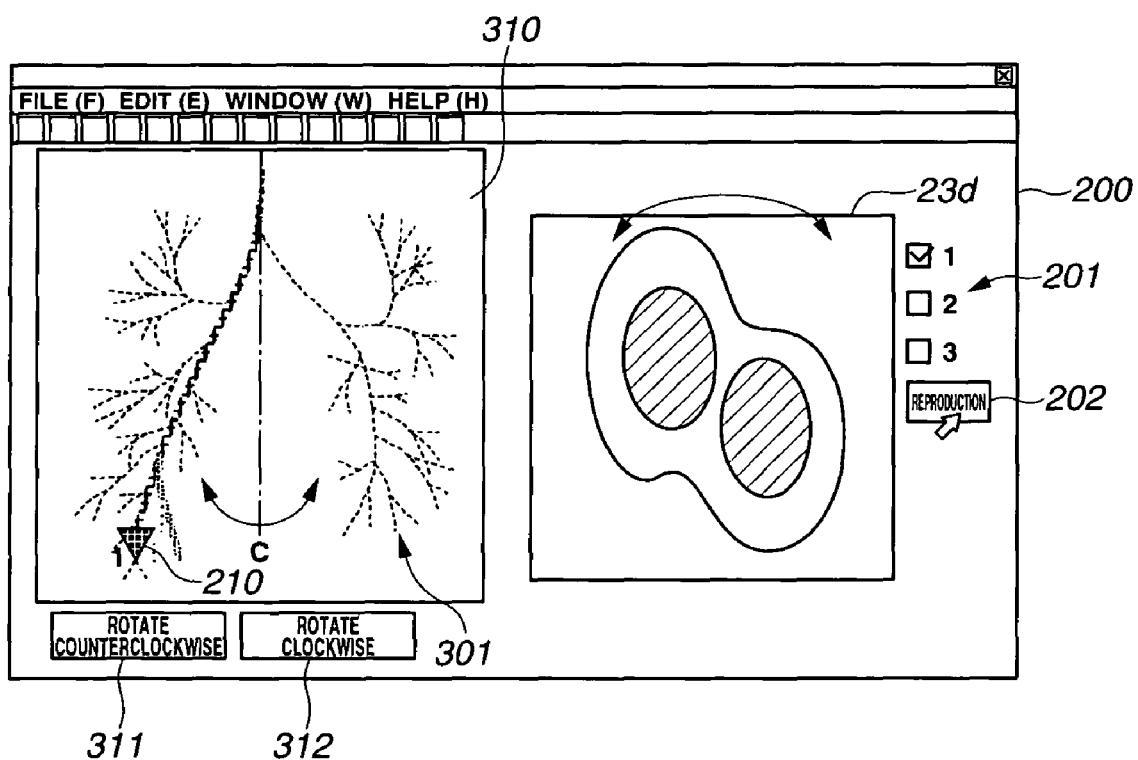
FIG. 36 is a fourth diagram describing operation of the route verification window in FIG. 31.

Similarly, upon the user clicking the reproduction button 202, for example, the pointer 210 positioned at the starting-point position as shown in FIG. 35 moves to the end-point position as shown in FIG. 36, and at this time, the VBS image is displayed on the VBS image display area 23d as a moving image in sync with this movement of the pointer 210.

Figure 37:
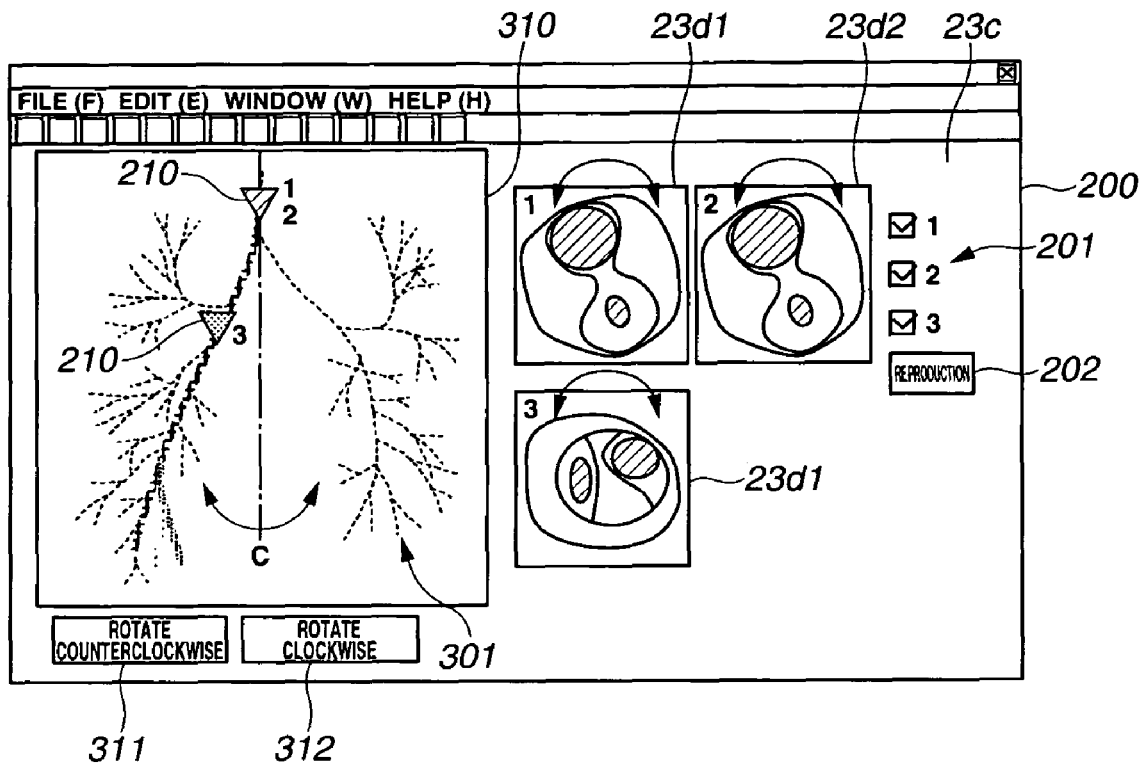
FIG. 37 is a fifth diagram describing operation of the route verification window in FIG. 31.

Further, as shown in FIG. 37, upon the user selecting three insertion routes at the checkboxes 201 for example, the respective pointers 210 are displayed on the thinning model image 301. Note that display of the VBS images is the same as in the case of operating the pointer 210 on an insertion route on an MPR image, and the route verification window 200 in a format shown in FIG. 37 is used for up to four insertion routes.

Figure 38:
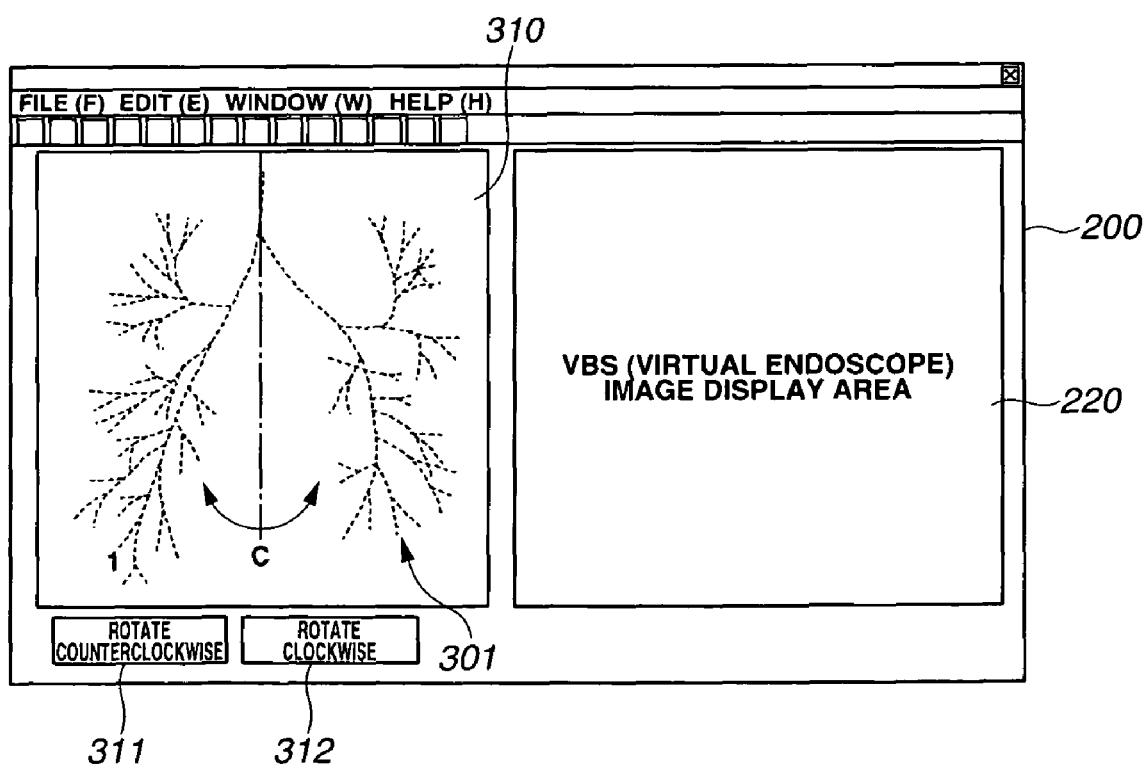
FIG. 38 is a sixth diagram describing operation of the route verification window in FIG. 31.

When the number of insertion routes is five or more, as shown in FIG. 38, the VBS display frame 220 is displayed on the route verification window 200, but this VBS display frame 220 has been described above, so description thereof will be omitted.

Figure 39:
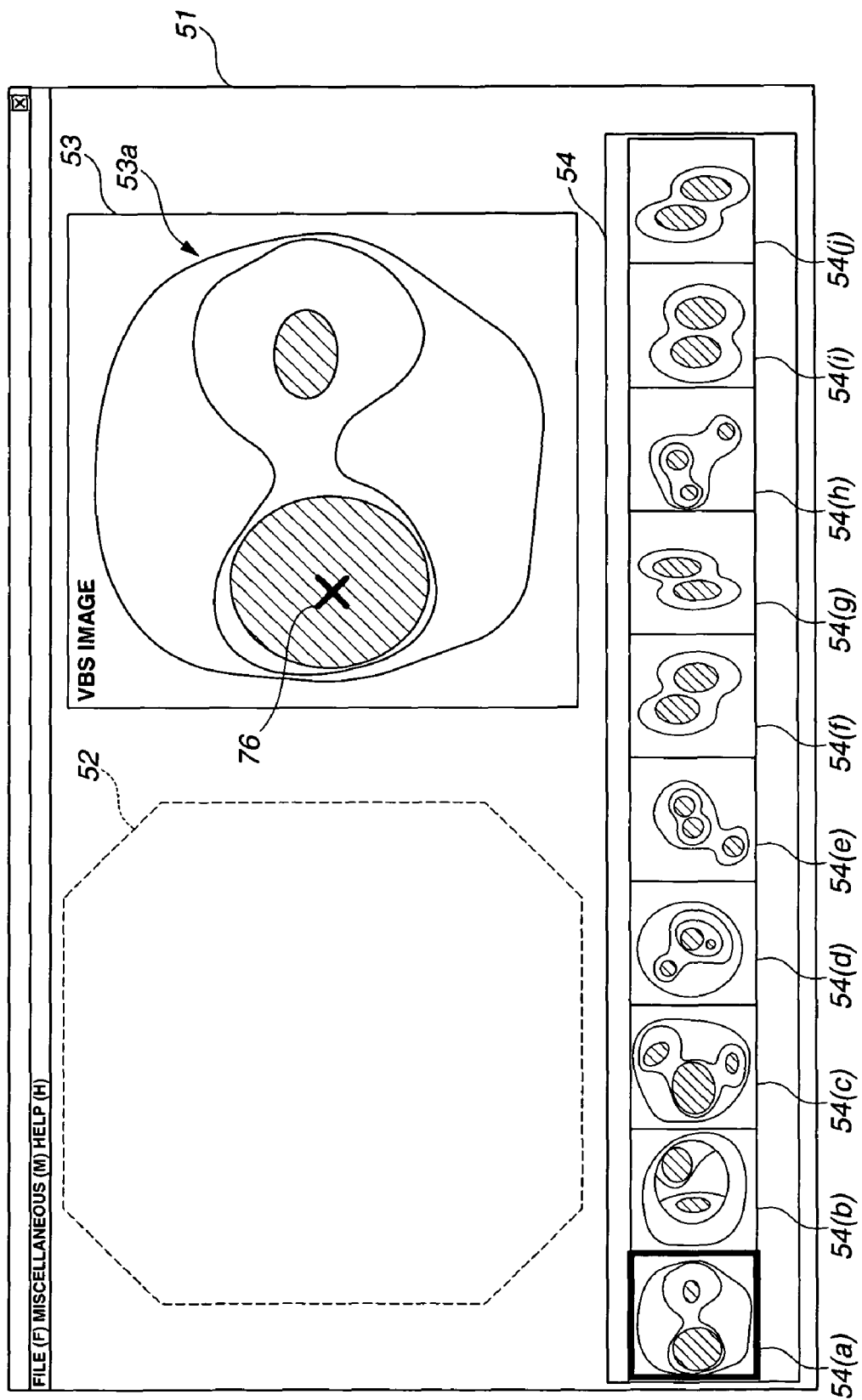
FIG. 39 is a diagram illustrating the insertion support screen to be developed in the processing in FIG. 2.

Thus, when starting bronchial tube endoscopy under the insertion support by the insertion support device 5 with the most appropriate support route selected by the route verifying function 14d, an insertion support screen 51 such as shown in FIG. 39 is displayed on the monitor 7. Note that the same insertion support screen 51 as the monitor 7 is also displayed on the monitor 6.

This insertion support screen 51 has an endoscope live image display area 52 for displaying the live image from the bronchoscope apparatus 3, a VBS image display area 53 for displaying a VBS image 53a, and a branch thumbnail VBS image area 54 for compressing the VBS image 53a at all of the branches of a route, and displaying these as reduced branch thumbnail VBS images 54(a) through 54(j), and the VBS image 53a serving as a virtual image corresponding to the branch point where the live image is positioned is displayed on the VBS image display area 53.

The frame of the same branch thumbnail VBS image as the VBS image 53a to be displayed on the VBS image display area 53 is displayed with a thick frame or in color, so can be distinguished from the other branch thumbnail VBS images, and the user can readily recognize which branch the VBS image to be displayed on the VBS image display area 53 belongs to.

Second Embodiment

The second embodiment is almost the same as the first embodiment, so only different points will be described, the same configurations are appended with the same reference numerals, and the description thereof will be omitted.

The route verifying function 14d of the route setting unit 14 according to the second embodiment has a route setting simulation function. The route setting simulation function compares the similarities between the structure of the bronchial tube of a patient serving as the target and the past bronchial tube structure data following completion of route setting. Subsequently, in the event that the CT-image-data storing unit 12 has bronchial tube structure data similar to the present target by more than a predetermined similarity, and also the VBS image storing unit 16 has operating data on the insertion support screen 51 when insertion support has a similar endpoint, the route setting simulation function displays the effect. This enables insertion support simulation using the bronchial tube structure data and operating data to be performed, and also allows the operator to perform verification of a route which has been set appropriately.

Figure 40:
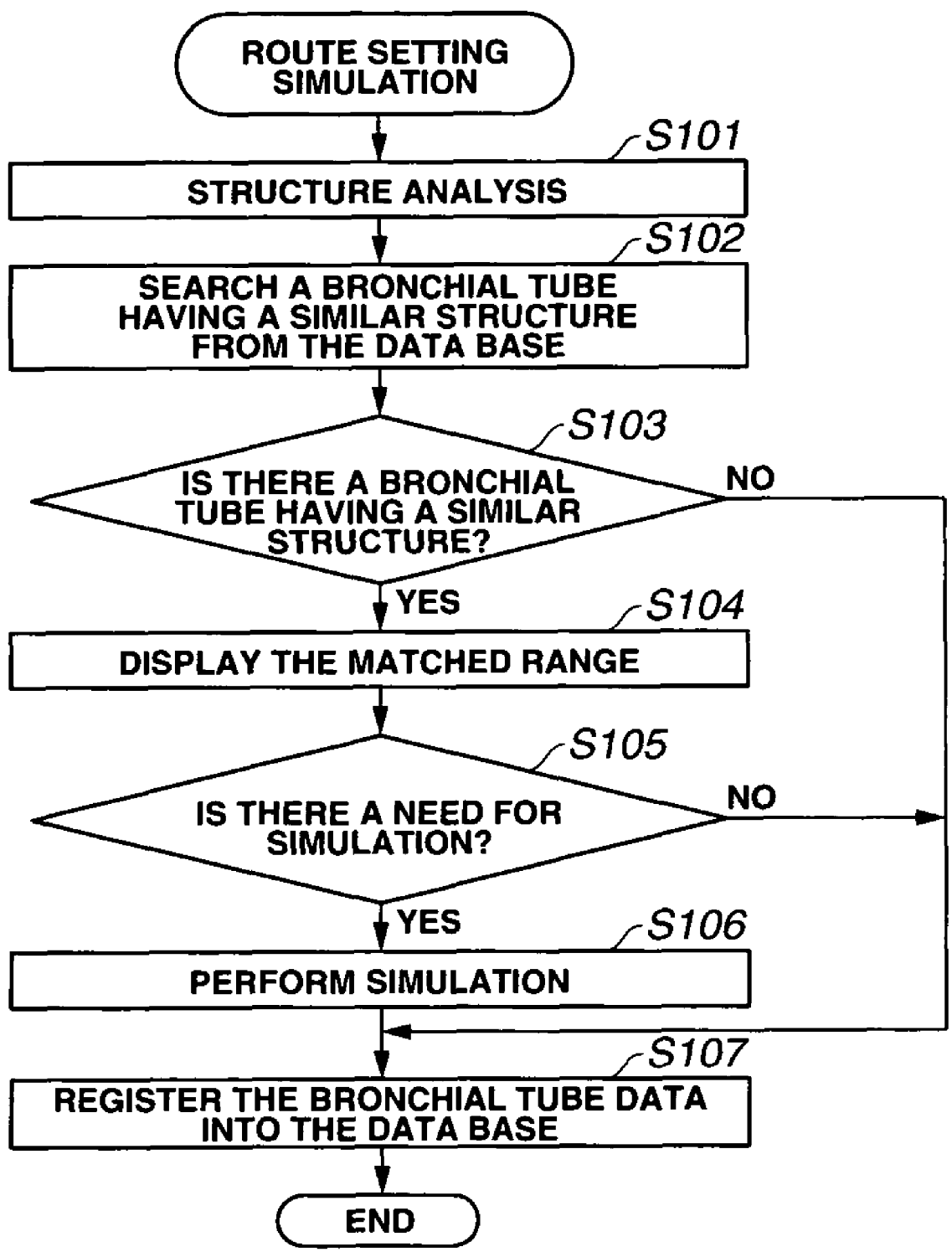
FIG. 40 is a flowchart illustrating the flow of route setting simulation processing using a route verifying function according to a second embodiment of the present invention.

Specifically, as shown in FIG. 40, the route verifying function 14d analyzes the bronchial tube structure of the target patient stored in the CT-image-data storing unit 12 in step S101, and searches the bronchial tube structure data having a similar structure from a database made up of the past bronchial tube structure data built on the CT-image-data storing unit 12 in step S102.

Figure 41:
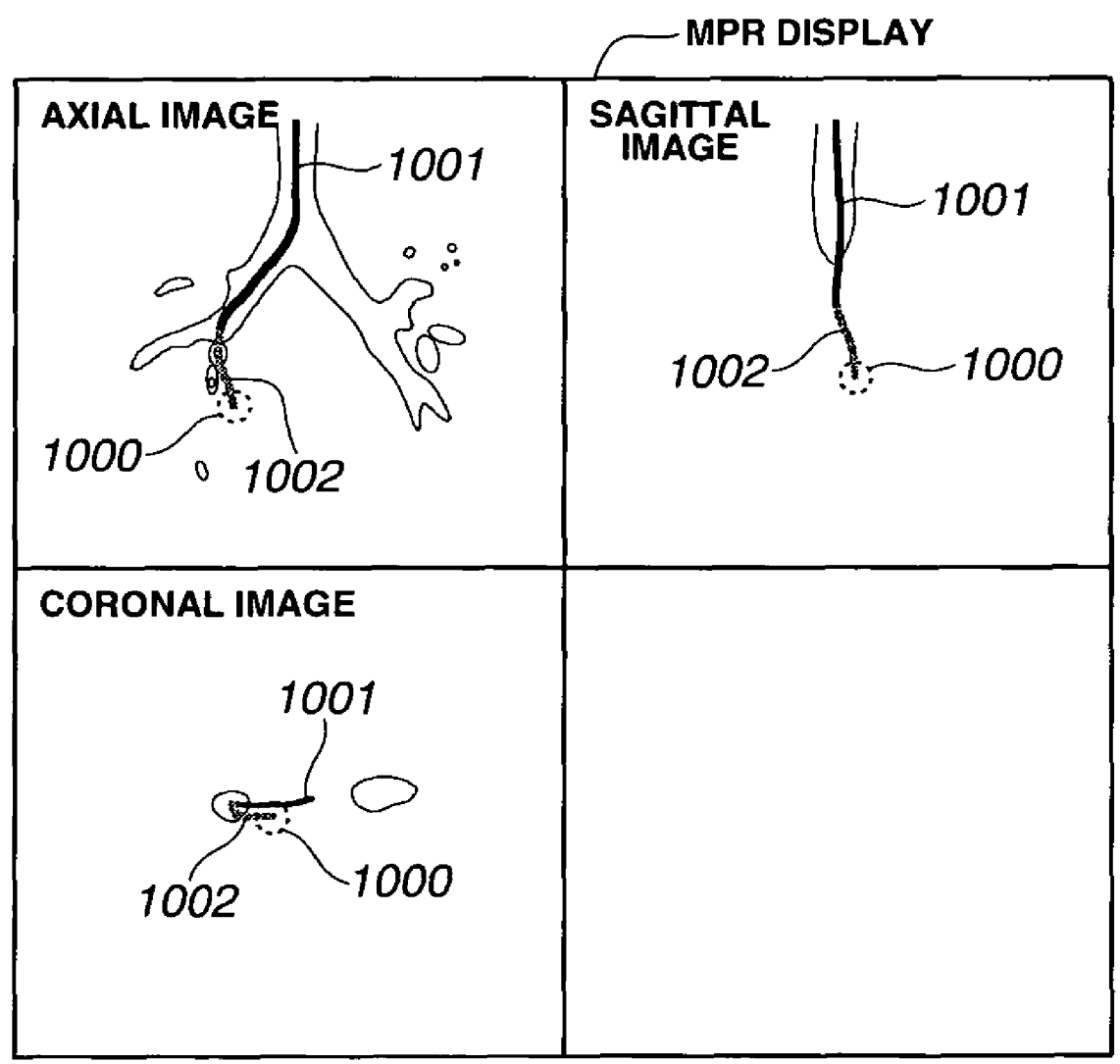
FIG. 41 is a first diagram describing the route setting simulation processing in FIG. 40.
Figure 42:
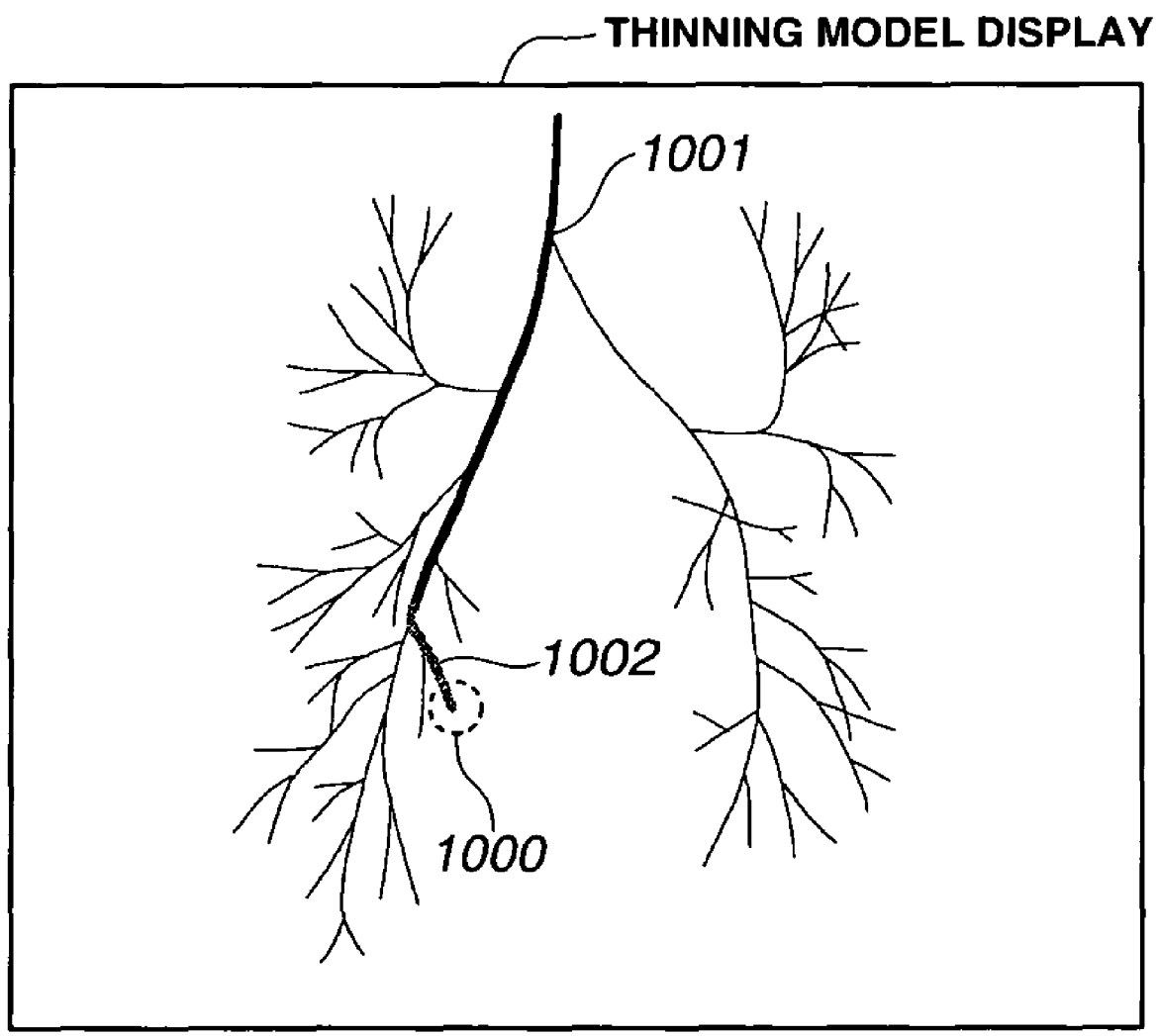
FIG. 42 is a second diagram describing the route setting simulation processing in FIG. 40.
Figure 43:
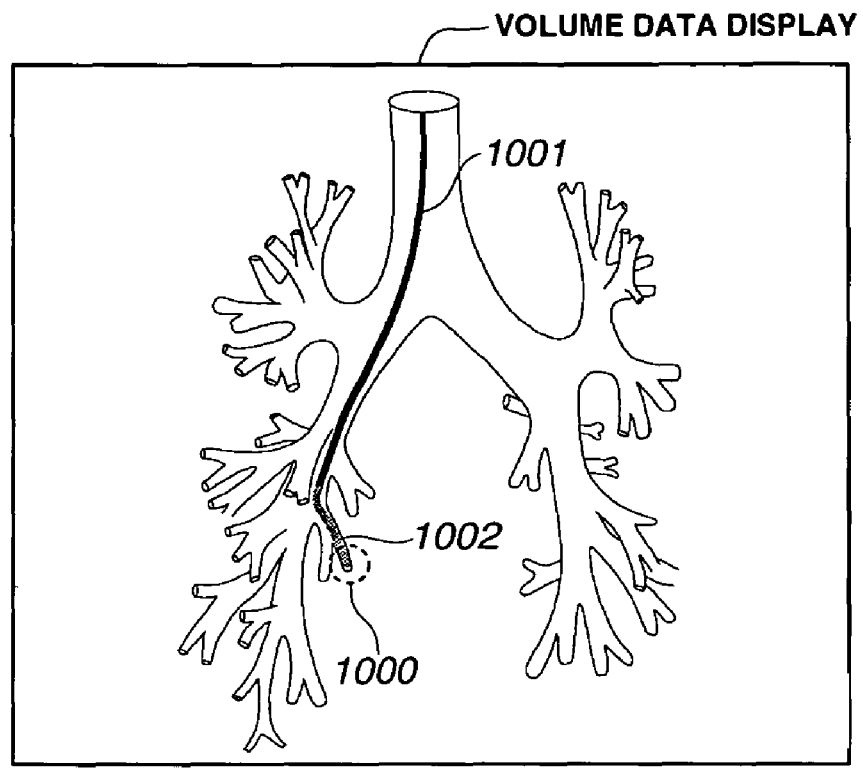
FIG. 43 is a third diagram describing the route setting simulation processing in FIG. 40.

Subsequently, in step S103, the route verifying function 14d determines whether or not there is a past bronchial tube structure data similar to that of the target patient by more than a predetermined similarity, and in the event that there is the past bronchial tube structure data, the route verifying function 14d displays the route range satisfying the condition of more than a predetermined similarity in step S104. Examples of a display method include, for example, route range display on each image such as:
(1) On an MPR image such as shown in FIG. 41
(2) On a thinning model image such as shown in FIG. 42
(3) On a volume data image such as shown in FIG. 43
Note that on each image in FIG. 41 through FIG. 43 a matched route range 1001 and an unmatched route range 1002 are displayed with a different color on the route toward an end-point range 1000.

Figure 44:
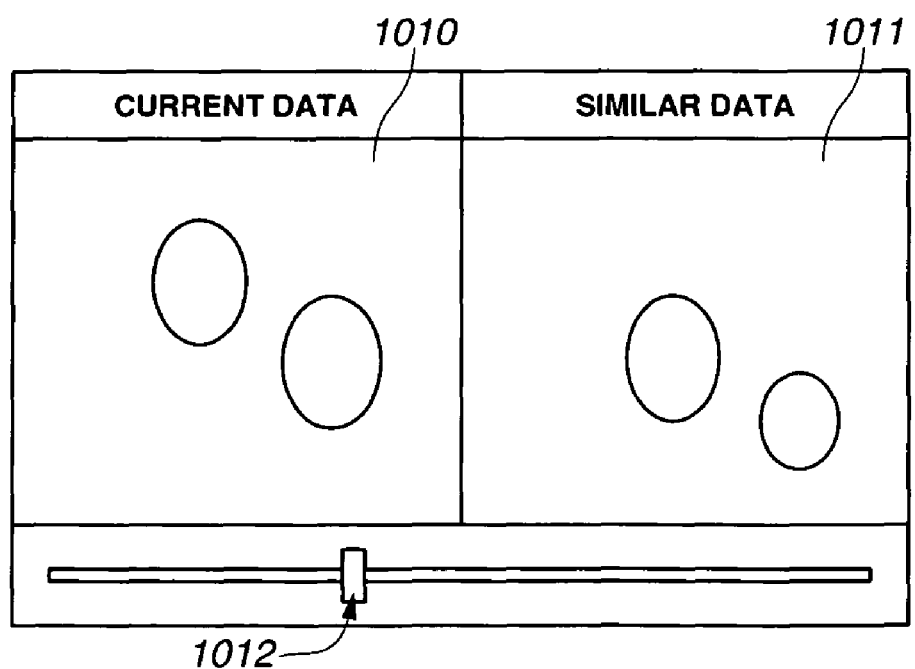
FIG. 44 is a fourth diagram describing the route setting simulation processing in FIG. 40.

Subsequently, in step S105 the route verifying function 14d determines whether or not a simulation using a VBS image based on the past bronchial tube structure data as to the route displayed should be performed, and upon the route verifying function 14d performing the simulation, the route verifying function 14d performs the simulation using comparative display between the VBS image of the target patient and the past VBS image within the matched route range like the VBS image such as shown in FIG. 44 in step S106, and in step S107 registers the past bronchial tube structure data into the database of the CT-image-data storing unit 12 as simulation target data, and ends the processing.

Note that FIG. 44 illustrates a screen made up of a first VBS image display area 1010 for displaying the VBS image of the target patient (current data), a second VBS image display area 1011 for displaying similar VBS image (past data), and a slider bar 1012 for specifying the display frame of these VBS images.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An insertion support system comprising:
a virtual image generating portion for generating a virtual image of a body cavity path within a subject based on the image data of a three-dimensional region of the subject;
a route starting-point setting portion for setting a starting-point of an insertion route of an endoscope to the body cavity path within the subject;
a region-of-interest setting portion for setting a region of interest within the subject;
a route extracting portion for extracting a plurality of insertion routes to a position of the body cavity path positioned near the region of interest from the starting-point; and
a route verifying portion for verifying the plurality of insertion routes extracted by the route extracting portion,
wherein the route verifying portion includes:
a position specifying portion for specifying an arbitrary position on the insertion route extracted by the route extracting portion; and
a display portion for displaying the virtual image in the position specified by the position specifying portion.

2. The insertion support system according to claim 1, comprising a position moving portion for moving the position specified by the position specifying portion.

3. An insertion support system comprising:
a virtual image generating portion for generating a virtual image of a body cavity path within a subject based on the image data of a three-dimensional region of the subject;
a route starting-point setting portion for setting a starting-point of an insertion route of an endoscope to the body cavity path within the subject;
a region-of-interest setting portion for setting a region of interest within the subject;
a route extracting portion for extracting a plurality of insertion routes to the region of interest from the starting-point; and
a route verifying portion for verifying the plurality of insertion routes extracted by the route extracting portion,
wherein the route verifying portion includes:

a position specifying portion for specifying an arbitrary position on the insertion route extracted by the route extracting portion; and a display portion for displaying the virtual image in the position specified by the position specifying portion and displaying the insertion route extracted by the route extracting portion on a multistage surface restructuring image based on the image data of the three-dimensional region.

4. An insertion support system comprising:

a virtual image generating portion for generating a virtual image of a body cavity path within a subject based on the image data of a three-dimensional region of the subject;

a route starting-point setting portion for setting a starting-point of an insertion route of an endoscope to the body cavity path within the subject;

a region-of-interest setting portion for setting a region of interest within the subject;

a route extracting portion for extracting a plurality of insertion routes to the region of interest from the starting-point; and a route verifying portion for verifying the plurality of insertion routes extracted by the route extracting portion, wherein the route verifying portion includes:

a position specifying portion for specifying an arbitrary position on the insertion route extracted by the route extracting portion; and a display portion for displaying the virtual image in the position specified by the position specifying portion and displaying the insertion route extracted by the route extracting portion on the three-dimensional restructuring image of the body cavity path within the subject based on the image data of the three-dimensional region.

\* \* \* \* \*